(12) United States Patent
Zhang et al.

(10) Patent No.: US 12,076,399 B2
(45) Date of Patent: *Sep. 3, 2024

(54) COMBINATION THERAPIES FOR TREATING CANCERS

(71) Applicant: Cothera Bioscience, Inc., Grand Cayman (KY)

(72) Inventors: Yihong Zhang, Calabasas, CA (US); Wang Wei, Beijing (CN); Yiyou Chen, San Jose, CA (US)

(73) Assignee: Cothera Bioscience, Inc., Grand Cayman (KY)

( * ) Notice: Subject to any disclaimer, the term of this patent is extended or adjusted under 35 U.S.C. 154(b) by 255 days.

This patent is subject to a terminal disclaimer.

(21) Appl. No.: 16/617,229

(22) PCT Filed: Jun. 1, 2018

(86) PCT No.: PCT/US2018/035641
§ 371 (c)(1),
(2) Date: Nov. 26, 2019

(87) PCT Pub. No.: WO2018/223022
PCT Pub. Date: Dec. 6, 2018

(65) Prior Publication Data
US 2020/0147211 A1    May 14, 2020

(30) Foreign Application Priority Data

Jun. 2, 2017  (WO) ................ PCT/CN2017/086911

(51) Int. Cl.
| | |
|---|---|
| *A61K 39/395* | (2006.01) |
| *A61K 31/4184* | (2006.01) |
| *A61K 31/4523* | (2006.01) |
| *A61K 31/506* | (2006.01) |
| *A61K 31/519* | (2006.01) |
| *A61K 45/06* | (2006.01) |
| *A61P 35/00* | (2006.01) |
| *C07K 16/22* | (2006.01) |
| *C07K 16/40* | (2006.01) |

(52) U.S. Cl.
CPC ...... *A61K 39/3955* (2013.01); *A61K 31/4184* (2013.01); *A61K 31/4523* (2013.01); *A61K 31/506* (2013.01); *A61K 31/519* (2013.01); *A61K 45/06* (2013.01); *A61P 35/00* (2018.01); *C07K 16/22* (2013.01); *C07K 16/40* (2013.01)

(58) Field of Classification Search
CPC ................ A61K 39/3955; A61K 35/00; A61K 31/4184; A61K 31/4523; A61K 31/506; A61K 31/519; A61K 45/06; C07K 16/22; C07K 16/40

See application file for complete search history.

(56) References Cited

U.S. PATENT DOCUMENTS

| | | | |
|---|---|---|---|
| 5,844,093 A | 12/1998 | Kettleborough et al. | |
| 6,734,203 B2 | 5/2004 | Matsuhisa et al. | |
| 7,132,511 B2 | 11/2006 | Carr et al. | |
| 7,247,301 B2 | 7/2007 | van de Winkel et al. | |
| 7,595,378 B2 | 9/2009 | van de Winkel et al. | |
| 7,618,992 B2 | 11/2009 | Nakahara et al. | |
| 7,723,484 B2 | 5/2010 | Beidler et al. | |
| 7,939,072 B2 | 5/2011 | Yarden et al. | |
| 7,960,516 B2 | 6/2011 | Matheus et al. | |
| 8,003,105 B2 | 8/2011 | Nakahara et al. | |
| 9,662,329 B2 | 5/2017 | Chang et al. | |
| 9,737,535 B2 | 8/2017 | Fultz et al. | |
| 10,004,735 B2 | 6/2018 | Fultz et al. | |
| 2003/0114508 A1 | 6/2003 | Matsuhisa et al. | |
| 2005/0222163 A1 | 10/2005 | Eck et al. | |
| 2006/0223831 A1 | 10/2006 | Kinoyama et al. | |
| 2006/0257895 A1 | 11/2006 | Pinkel et al. | |
| 2008/0166344 A1 | 7/2008 | Nakahara et al. | |
| 2009/0124595 A1 | 5/2009 | Adams et al. | |
| 2009/0246198 A1 | 10/2009 | Dong et al. | |
| 2009/0263390 A1 | 10/2009 | Nakahara et al. | |
| 2010/0004234 A1 | 1/2010 | Santi et al. | |
| 2010/0249413 A1 | 9/2010 | Murai et al. | |
| 2012/0028907 A1 | 2/2012 | Shackney | |
| 2012/0122910 A1 | 5/2012 | Berezov et al. | |
| 2013/0035336 A1 | 2/2013 | Borland et al. | |
| 2014/0199236 A1 | 7/2014 | Chen et al. | |
| 2014/0271634 A1* | 9/2014 | Sliwkowski | A61K 31/437 424/133.1 |

(Continued)

FOREIGN PATENT DOCUMENTS

| | | |
|---|---|---|
| CA | 2 943 402 A1 | 10/2015 |
| CN | 101910167 A | 12/2010 |

(Continued)

OTHER PUBLICATIONS

Berenbaum et al, Clin exp Immunol, 1997, 28:1-18 (Year: 1997).*
Wiesenthal, Human Tumor Assay Journal, on-line at (http://weisenthal.org/synergy1.htm), Mar. 14, 2012 (Year: 2012).*
Extended European Search Report dated Jan. 22, 2021 for European Application No. 18810472.3, 7 pages.
International Search Report and Written Opinion mailed Nov. 12, 2020 for International Application No. PCT/CN2020/074515, 13 pages.
International Search Report and Written Opinion mailed Apr. 27, 2021 for International Application No. PCT/US2021/16861, 10 pages.
International Search Report and Written Opinion mailed Nov. 10, 2020 for International Application No. PCT/CN2020/074516, 13 pages. I (Continued)

*Primary Examiner* — Mark Halvorson
*Assistant Examiner* — Dennis J Sullivan
(74) *Attorney, Agent, or Firm* — COOLEY LLP

(57) ABSTRACT

Provided are combination therapies and related compositions and methods for treating cancers, including epithelial tumors, which include a combination of at least two agents such as an epidermal growth factor receptor (EGFR) inhibitor, a mitogen-activated protein kinase (MEK) 1/2 inhibitor; and a cyclin dependent kinase (CDK) 4/6 inhibitor.

9 Claims, 1 Drawing Sheet

(56) References Cited

U.S. PATENT DOCUMENTS

| | | | |
|---|---|---|---|
| 2014/0314749 A1 | 10/2014 | French et al. | |
| 2016/0024591 A1 | 1/2016 | Xu et al. | |
| 2016/0095942 A1 | 4/2016 | Markovic et al. | |
| 2016/0228457 A1 | 8/2016 | Chigaev et al. | |
| 2016/0317538 A1 | 11/2016 | Saha et al. | |
| 2016/0367663 A1 | 12/2016 | Doshi et al. | |
| 2017/0027951 A1 | 2/2017 | Klampfer | |
| 2017/0080093 A1* | 3/2017 | Hoffman | A61K 47/55 |
| 2017/0114098 A1 | 4/2017 | Aivado et al. | |
| 2019/0046529 A1 | 2/2019 | Quayle et al. | |
| 2019/0292602 A1 | 9/2019 | Chapuy et al. | |
| 2021/0180141 A1 | 6/2021 | Li et al. | |

FOREIGN PATENT DOCUMENTS

| | | | |
|---|---|---|---|
| CN | 106822905 A | 6/2017 | |
| CN | 107708734 A | 2/2018 | |
| EP | 1747784 A1 | 1/2007 | |
| EP | 2 127 652 A1 | 12/2009 | |
| JP | 2017502013 A | 1/2017 | |
| JP | 2017511341 A | 4/2017 | |
| KR | 2014-0131827 A | 11/2014 | |
| WO | WO 01/60803 A1 | 8/2001 | |
| WO | WO 2004/092160 A1 | 10/2004 | |
| WO | WO-2005052005 A1 | 6/2005 | |
| WO | WO-2007086342 A1 | 8/2007 | |
| WO | WO 2007/140222 A2 | 12/2007 | |
| WO | WO-2008054701 A1 | 5/2008 | |
| WO | WO 2008/023807 A1 | 1/2010 | |
| WO | WO 2010/020675 A1 | 2/2010 | |
| WO | WO 2008/081927 A1 | 4/2010 | |
| WO | WO-2011106298 A1 | 9/2011 | |
| WO | WO-2012022724 A1 | 2/2012 | |
| WO | WO 2012/161177 A1 | 11/2012 | |
| WO | WO 2012/167099 A1 | 12/2012 | |
| WO | WO-2013034806 A1 | 3/2013 | |
| WO | WO 2013/074596 A1 | 5/2013 | |
| WO | WO-2013060872 A1 | 5/2013 | |
| WO | WO 2013/148649 A1 | 10/2013 | |
| WO | WO-2014018725 A1 | 1/2014 | |
| WO | WO 2014/147573 A3 | 9/2014 | |
| WO | WO-2015095840 A1 | 6/2015 | |
| WO | WO-2015150826 A1 | 10/2015 | |
| WO | WO-2015193212 A1 | 12/2015 | |
| WO | WO 2016/191296 A1 | 12/2016 | |
| WO | WO 2016/201370 A1 | 12/2016 | |
| WO | WO-2016201370 A1 * | 12/2016 | A61K 31/4162 |
| WO | WO-2017019279 A1 | 2/2017 | |
| WO | WO 2017/037576 A1 | 3/2017 | |
| WO | WO-2017048800 A1 | 3/2017 | |
| WO | WO 2017/070675 A1 | 4/2017 | |
| WO | WO 2017/120439 A1 | 7/2017 | |
| WO | WO-2018054348 A1 | 3/2018 | |
| WO | WO 2018/127786 A1 | 7/2018 | |
| WO | WO-2018218633 A1 | 12/2018 | |
| WO | WO-2018223022 A1 | 12/2018 | |
| WO | WO-2019195959 A1 | 10/2019 | |
| WO | WO 2020/034061 A1 | 2/2020 | |
| WO | WO 2020/036852 A1 | 2/2020 | |
| WO | WO 2020/097901 A1 | 5/2020 | |

OTHER PUBLICATIONS nternational Search Report and Written Opinion mailed Apr. 22, 2021 for International Application No. PCT/2021/016863, 12 pages.

International Search Report and Written Opinion mailed Jun. 21, 2021 for International Application No. PCT/CN2020/117167, 14 pages.

Aburjania, Z. et al., "The Role of Notch3 in Cancer," The Oncologist, 23:900-911 (2018).

Asahi, M. et al., "YM155 suppresses proliferation and survival of multiple myeloma cells via proteasomal degradation of c-Myc.," J Mec Oncl Ther, 1(2):62-71 (2016).

Ashworth, T. D. et al., "Deletion-based mechanisms of Notch1 activation in T-ALL: key roles for RAG recombinase and a conserved internal translational start site in Notch1," Blood, 116(25):5455-5464 (2010).

Beltran, H., "The N-myc Oncogene: Maximizing its Targets, Regulation, and Therapeutic Potential," Mol Cancer Res, 12(6):815-822 (2014).

Boskovski, M. T. et al., "The heterotaxy gene GALNT11 glycosylates Notch to orchestrate cilia type and laterality," Nature, 504:456-459 (2013), including Methods and Extended Data, 11 pages.

Bundgaard, H., "Design of Prodrugs," pp. 7-9; 21-24, Elsevier Science Publishers, Amsterdam, 1985, 10 pages.

CAS Registry No. 781661-94-7, Nov. 16, 2004, 3 pages.

Cheng, X. J. et al., "Survivin inhibitor YM155 suppresses gastric cancer xenograft growth in mice without affecting normal tissues," Oncotarget, 7(6):7096-7109 (2016).

Cheson, B. D. et al., "Abstract 8502. Safety and efficacy of YM155 in diffuse large B-cell lymphoma (DLBCL)," Journal of Clinical Oncology, No. 15, Suppl vol. 27 (2009), 2 pages.

Coiffier, B. & Sarkozy, C., "Diffuse large B-cell lymphoma: R-CHOP failure—what to do?" Hematology Am Soc Hematol Educ Program, (1):366-378 (2016).

Darzynkiewicz, Z. et al., "Flow Cytometry in Analysis of Cell Cycle and Apoptosis," Semin Hematol, 38:179-193 (2001).

Ellisen, L. W. et al., "TAN-1, the Human Homolog of the *Drosophila* Notch Gene, Is Broken by Chromosomal Translocations in T Lymphoblastic Neoplasms," Cell, 66:649-661 (1991).

Ferrarotto, R. et al., "Activating NOTCH1 Mutations Define a Distinct Subgroup of Patients With Adenoid Cystic Carcinoma Who Have Poor Prognosis, Propensity to Bone and Liver Metastasis, and Potential Responsiveness to Notch1 Inhibitors," Journal of Clinical Oncology, 35(3):352-360 (2016).

Gautam, P. et al., "Identification of selective cytotoxic and synthetic lethal drug responses in triple negative breast cancer cells," Molecular Cancer, 15:34 (2016), 16 pages; doi. 10.1186/s12943-016-0517-3.

Haydu, J. E. et al., "An activating intragenic deletion in NOTCH1 in human T-ALL," Blood, 119(22):5211-5214 (2012).

Kawazu, M. et al., "Integrative analysis of genomic alterations in triple-negative breast cancer in association with homologous recombination deficiency," PLoS Genet, 13(6):e1006853 (2017), 23 pages; https://doi.org/10.1371/journal.pgen.1006853.

Liu, Z. et al., "Prognostic and biological significance of survivin expression in patients with diffuse large B-cell lymphoma treated with rituximab-CHOP therapy," Mod Pathol, (10):1297-314 (2015); doi:10.1038/modpathol.2015.94.

Minematsu, T. et al., "Carrier-Mediated Uptake of 1-(2-Methoxyethyl)-2-methyl-4,9-dioxo-3-(pyrazin-2-ylmethyl)-4,9-dihydro-1H-naphtho[2,3-d]imidazolium Bromide (YM155 Monobromide), a Novel Small-Molecule Survivin Suppressant, into Human Solid Tumor and Lymphoma Cells," Drug Metabolism and Disposition, 37(3):619-628 (2009).

Na, Y-S. et al., "YM155 Induces EGFR Suppression in Pancreatic Cancer," PLoS One, 7(6):e38625 (2012), 10 pages; doi:10.1371/journal.pone/0038625.

Nakahara, T. et al., "YM155, a Novel Small-Molecule Survivin Suppressant, Induces Regression of Established Human Hormone-Refractory Prostate Tumor Xenografts," Cancer Res, 67(17):8014-8021 (2007).

O'Neil, J. et al., "FBW7 mutations in leukemic cells mediate NOTCH pathway activation and resistance to γ-secretase inhibitors," JEM, 204(8):1813-1824 (2007).

Parra, I. & Windle, B., "High resolution visual mapping of stretched DNA by fluorescent hybridization," Nature Genetics, 5:17-21 (1993).

Pinkel, D. & Albertson, D. G., "Comparative Genomic Hybridization," Annu. Rev. Genomics Hum. Genet., 6:331-354 (2005).

Puentes, X. S. et al., "Non-coding recurrent mutations in chronic lymphocytic leukaemia," Nature, 526:519-524 (2015), including Methods, 5 pages.

Radic-Sarikas, B. et al., "Lapatinib potentiates cytotoxicity of YM155 in neuroblastoma via inhibition of the ABCB1 efflux transporter," Scientific Reports, 7:3091 (2017), 8 pages; doi:10.1038/s41598-017-03129-6.

(56) References Cited

OTHER PUBLICATIONS

Rosati, E. et al., "NOTCH1 Aberrations in Chronic Lymphocytic Leukemia," Front. Oncol., 8:229 (2018), 20 pages; doi:10.3389/fonc.2018.00229.
Schouten, J. P. et al., "Relative quantification of 40 nucleic acid sequences by multiplex ligation-dependent probe amplification," Nucleic Acids Research, 30(12):e57 (2002), 13 pages.
Sulis, M. L. et al., "NOTCH1 extracellular juxtamembrane expansion mutations in T-ALL," Blood, 112:733-740 (2008).
Thompson, B. J. et al., "The SCF$^{FBW7}$ ubiquitin ligase complex as a tumor suppressor in T cell leukemia," JEM, 204(8):1825-1835 (2007).
UniProtKB No. P46531, Apr. 7, 2021, 22 pages.
Warrier, N. M. et al., "Emerging Importance of Survivin in Stem Cells and Cancer: the Development of New Cancer Therapeutics," Stem Cell Reviews and Reports, 16:828-852 (2020).
Van Agthoven, M. et al., "A review of recruitment criteria, patient characteristics and results of CHOP chemotherapy in prospective randomized phase III clinical trials for aggressive non-Hodgkin's lymphoma," The Hematology Journal, 4:399-409 (2003).
Wang, K. et al., "PEST Domain Mutations in Notch Receptors Comprise an Oncogenic Driver Segment in Triple-Negative Breast Cancer Sensitive to a γ-Secretase Inhibitor," Clin Cancer Res, 21(6):1487-1496 (2015).
Weng, A. P. et al., "Activating Mutations of NOTCH1 in Human T Cell Acute Lymphoblastic Leukemia," Science, 306:269-271 (2004).
Westhoff, B. et al., "Alterations of the Notch pathway in lung cancer," PNAS, 106(52):22293-22298 (2009).
Woo, S. M. et al., "YM155 enhances ABT-737-mediated apoptosis through Mcl-1 downregulation in Mcl-1-overexpressed cancer cells," Mol Cell Biochem, 429:91-102 (2017).
Yamanaka, K. et al., "YM155, a selective survivin suppressant, inhibits tumor spread and prolongs survival in a spontaneous metastatic model of human triple negative breast cancer," International Journal of Oncology, 39:569-575 (2011).
Ye, B. H. et al., "Alterations of a Zinc Finger-Encoding Gene, BCL-6, in Diffuse Large-Cell Lymphoma," Science, 262:747-750 (1993).
Zhao, M. et al., "Computational tools for copy number variation (CNV) detection using next-generation sequencing data: features and perspectives," BMC Bioinformatics, 14(Suppl 11):S1 (2013), 16 pages; http://www.biomedcentral.com/1471-2105/14/S11/S1.
Zhao, X. et al., "Survivin Inhibition Is Critical for Bcl-2 Inhibitor-Induced Apoptosis in Hepatocellular Carcinoma Cells," PLoS One, 6(8):e21980 (2011), 9 pages; doi:10.1371/journal.pone.0021980.
Zhong, Y. et al., "NOTCH 1 is a poor prognostic factor for breast cancer and is associated with breast cancer stem cells," Oncotargets and Therapy, 9:6865-6871 (2016).
International Search Report and Written Opinion mailed Mar. 8, 2018 for International Application No. PCT/CN2017/086911, 12 pages.
International Search Report and Written Opinion mailed Aug. 31, 2018 for International Application No. PCT/US2018/035641, 9 pages.
Luke, J. J. et al., "The Biology and Clinical Development of MEK Inhibitors for Cancer," Drugs, 74:2111-2128 (2014).
Thomas, A. et al., "Refining the treatment of NSCLC according to histological and molecular subtypes," Nature Reviews Clinical Oncology, 12:511-526 (2015).
Zhou, J. et al., "CDK4/6 or MAPK blockade enhances efficacy of EGFR inhibition in oesophageal squamous cell carcinoma," Nature Communications, 8: 13897 (2017), 12 pages; https://doi.org/10.1038/ncomms13897.
International Search Report and Written Opinion mailed Dec. 13, 2021 for International Application No. PCT/US2021/50657, 13 pages.
Aoyama, Y. et al., "Pharmacokinetics of sepantronium bromide (YM155), a small-molecule suppressor of survivin, in Japanese patients with advanced solid tumors: dose proportionality and influence of renal impairment," Cancer Chemother Pharmacol, 70:373-380 (2012).
Tao, Y.-F. et al., "Survivin selective inhibitor YM155 induce apoptosis in SK-NEP-1 Wilms tumor cells," BMC Cancer, 12:619 (2012), 13 pages; http://www.biomedcentral.com/1471-2407/12/619.
Adderley et al., (2019). "KRAS-mutant non-small cell lung cancer: Converging small molecules and immune checkpoint inhibition," EBioMedicine, 41:711-716.
Barras, (2015). "BRAF Mutation in Colorectal Cancer: An Update: Supplementary Issue: Biomarkers for Colon Cancer," Biomarkers in Cancer, 7:9-12.
Berge, S. M. et al., "Pharmaceutical Salts," J Pharm Sci, 66(1):1-19 (Jan. 1977).
Cantwell-Dorris, "BRAFV600E: Implications for Carcinogenesis and Molecular Therapy," Mol Cancer Ther., 10(3):385-394 (Mar. 2011).
Chapman, et al., "Improved Survival with Vemurafenib in Melanoma with BRAF V600E Mutation." N Eng J Med (2001); 364(26): 2507-2516.
Cheng et al., (2017). "Current Development Status of MEK Inhibitors," Molecules, 22:1551, 20 pages.
Cox, A., et al., "Drugging the undruggable Ras: mission possible?," Nat Rev Drug Discov., vol. 13(11): 828-851 (2014).
Davies, H. et al., "Mutations of the BRAF gene in human cancer," Nature 417: 949-54, 2002.
Extended European Search Report and Written Opinion mailed on Jan. 28, 2022, for European Patent Application No. 19784395.6, 8 pages.
Ferrer et al., (2018). "KRAS-Mutant non-small cell lung cancer: From biology to therapy," Lung Cancer, 124:53-64.
Hall et al., (2014). "BRAF mutations: signaling, epidemiology, and clinical experience in multiple malignancies," Cancer Control, 21:221-30.
Hyman et al., (2015). "Vemurafenib in Multiple Nonmelanoma Cancers with BRAF V600 Mutations," N. Engl. J. Med., 373:726-736.
International Search Report and Written Opinion mailed on Jan. 11, 2021, for PCT Patent Application No. PCT/CN2020/119873, 13 pages.
International Search Report and Written Opinion mailed on Jan. 8, 2019, for PCT Patent Application No. PCT/CN2018/082191, 11 pages.
International Search Report and Written Opinion mailed on Jan. 8, 2021, for PCT Patent Application No. PCT/CN2020/119874, 18 pages.
International Search Report and Written Opinion mailed on Mar. 9, 2018, for PCT Patent Application No. PCT/CN2017/086911, 12 pages.
International Search Report and Written Opinion mailed on Sep. 5, 2019, for PCT Patent Application No. PCT/CN2019/081674, 9 pages.
Jia et al., (2017). "Characterization of distinct types of KRAS mutation and its impact on first-line platinum-based chemotherapy in Chinese patients with advanced non-small cell lung cancer," Oncol. Lett., 14:6525-6532.
Larkin et al., (2014). "Combined Vemurafenib and Cobimetinib in BRAF-Mutated Melanoma," N. Engl. J. Med., 371:1867-1876.
Lasota et al., (2015). "Detection of the BRAF V600E mutation in colon carcinoma: critical evaluation of the immunohistochemical approach," Am J Surg Pathol., 38(9):1235-41, 16 pages.
Lee et al., (2016). "Efficacy of the combination of MEK and CDK4/6 inhibitors in vitro and in vivo in KRAS mutant colorectal cancer models," Oncotarget, 26(7):39595-39608.
Loupakis et al., (2014). "Initial Therapy with FOLFOXIRI and Bevacizumab for Metastatic Colorectal Cancer," N Engl J Med., 371:1609-1618.
Manzano et al., (2016). "Resistant mechanisms to BRAF inhibitors in melanoma," Ann. Transl Med, 4:237, 9 pages.
Martini et al., (2017). "Present and future of metastatic colorectal cancer treatment: A review of new candidate targets," World Journal Of Gastroenterology, 23(26):4675-4688.

(56) References Cited

OTHER PUBLICATIONS

Morikawa et. al., (2018). "BRAF V600E mutation is a predictive indicator of upfront chemotherapy for stage IV colorectal cancer," Oncology Lett., 15:2195-2201.

Morris et al., (2013). "BRAF inhibitors in clinical oncology," F1000Prime Rep., 5:11, 6 pages.

Mullard, (2019). "Cracking KRAS," Nature Reviews Drug Discovery, 18:887-891.

Oikonornou et al., (2014). "BRAF vs RAS oncogenes: Are mutations of the same pathway equal? Differential signalling and therapeutic implications," Oncotarget, 5:11752-11777.

Pek et al., (2017). "Oncogenic KRAS-associated gene signature defines co-targeting of CDK4/6 and MEK as a viable therapeutic strategy in colorectal cancer," Oncogene, 36:4975-4986.

Porru et al., (2018). "Targeting KRAS in metastatic colorectal cancer: current strategies and emerging opportunities," J Exp Clin Cancer Res., 37(1):57, 10 pages.

Riely et al., (2009). "KRAS mutations in non-small cell lung cancer," Proc Am Thorac Soc, 6:201-205.

Robert, C. et al. (Jan. 2015) "Improved Overall Survival in Melanoma with Combined Dabrafenib and Trametinib" The New England Journal of Medicine, 372:30-39.

Robert et al., (2011). "RAF inhibition and induction of cutaneous squamous cell carcinoma," Curr. Opin. Oncol., 23:177-182.

Roman et al., (2018). "KRAS oncogene in non-small cell lung cancer: clinical perspectives on the treatment of an old target," Mol Cancer, 17:33, 14 pages.

Roskoski, (2014). "The ErbB/HER family of protein-tyrosine kinases and cancer," Pharmacological Research, 79:34-74.

Roskoski, (2019). "Small molecule inhibitors targeting the EGFR/ErbB family of proteintyrosine kinases in human cancers," Pharmacological Research, 139:395-411.

Troiani et al., (2014)."Primary and acquired resistance of colorectal cancer cells to anti-EGFR antibodies converge on MEK/ERK pathway activation and can be overcome by combined MEK/EGFR inhibition," Clinical Cancer Research, 20(14):3775-3786.

Wang et al., (2020). "Conditionally reprogrammed colorectal cancer cells combined with mouse avatars identify synergy between EGFR and MEK or CDK4/6 inhibitors," American Journal of Cancer Research, 1(10):249-262.

Wu et al., (2020). "Effects of avitinib on the pharmacokinetics of osimertinib in vitro and in vivo in rats," Thoracic Cancer, 11(10):2775-2781.

Xing et al., (2005). "BRAF mutation in thyroid cancer," Endocr. Relat. Cancer, 12:245-62.

Xu et al., (2016). "Advances in small molecule kinase inhibitors for cancer treatment," Chinese Bulletin Of Life Sciences, 28(7):786-792, 15 pages. (English translation pp. 1-8, Original pp. 9-15).

Ziemke et al., (2015). "Sensitivity of KRAS-Mutant Colorectal Cancers to Combination Therapy That Cotargets MEK and CDK4/6," Clinical Cancer Research, 2(22):405-414.

Asahi M., et al., "YM155 Suppresses Proliferation and Survival of Multiple Myeloma Cells Viaproteasomal Degradation of c-Myc," Journal of Medical Oncology Therapy, Dec. 2016, vol. 1 (2), pp. 62-71.

Extended European Search Report dated Jun. 27, 2022 for European Application No. 19849633.3, 7 pages.

Hidehiro, T. et al., Abstract. "Low-level copy gain versus amplification of myc oncogenes in medulloblastoma: utility in predicting prognosis and survival. Laboratory investigation," J Neurosurg Pediatr, 3(1):61-5 (2009). doi: 10.3171/2008.10.PEDS08105, 1 page.

Maiello, M.R., et al., "EGFR and MEK Blockade in Triple Negative Breast Cancer Cells," Journal of Cellular Biochemistry, Dec. 2015, vol. 116(12), pp. 2778-2785.

Masuishi, T., et al., "Current Progress and Feasibility of Using Molecular-Targeted Agent Combinations for Metastatic Colorectal Cancer," Japanese Journal of Cancer and Chemotherapy, Apr. 2016, vol. 43(4), pp. 408-412.

Ohshima, K. et al., "Integrated analysis of gene expression and copy number identified potential cancerdriver genes with amplificationdependent overexpression in 1,454 solid tumors," Scientific Reports, 7:641 (2017), 13 pages; doi:0.1038/s41598-017-00219-3.

Voges, Y. et al., "Effects of YM155 on survivin levels and viability in neuroblastoma cells with acquired drug resistance," Cell Death and Disease, 6:e2410 (2016), 11 pages; doi.10.2038/cddis.2016.257.

Notice of Allowance mailed May 26, 2023 for U.S. Appl. No. 17/045,982, 13 pages.

Bliss, C. I., "The toxicity of poisons applied jointly," Ann. Appl. Biol., 26:585-615 (1939); 10.1111/j.1744-7348.1939.tb06990.x.

Tang, J. et al., "What is Synergy? The Saariselka agreement revisited," Front. Pharmacol., 6:181 (2015); doi:10.3389/fphar.2015.00181, 5 pages.

\* cited by examiner

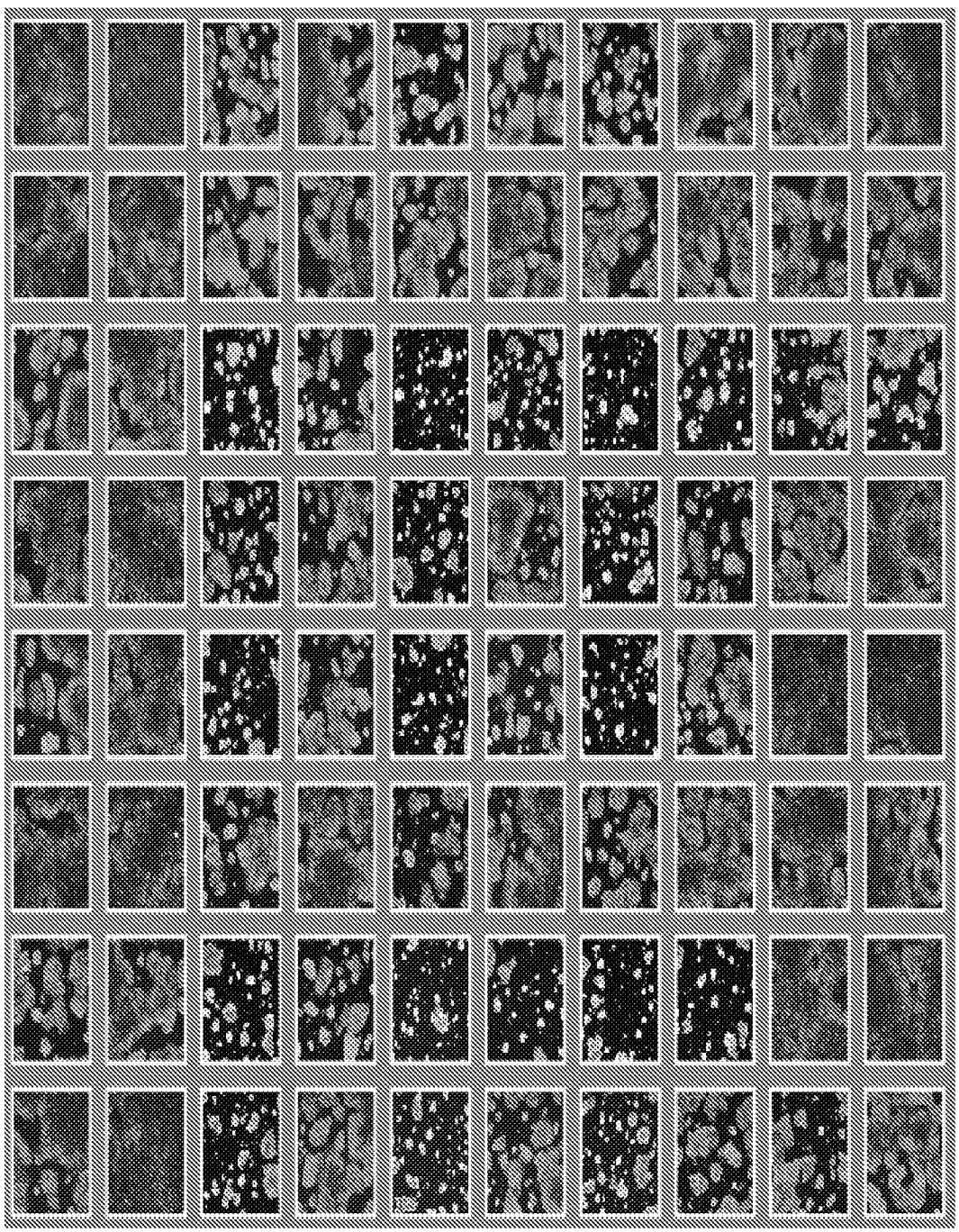

COMBINATION THERAPIES FOR TREATING CANCERS

This application is a § 371 national phase application of International Application No. PCT/US2018/035641, filed Jun. 1, 2018, which claims priority to PCT/CN2017/086911, filed 2 Jun. 2017, which is incorporated by reference in its entirety.

BACKGROUND

Technical Field

Embodiments of the present disclosure relate to combination therapies and related compositions and methods for treating cancers, including epithelial tumors, which include a combination of at least two agents such as an epidermal growth factor receptor (EGFR) inhibitor, a mitogen-activated protein kinase (MEK) 1/2 inhibitor, and a cyclin dependent kinase (CDK) 4/6 inhibitor.

BRIEF SUMMARY

Embodiments of the present disclosure relate, in pertinent part, to methods of treating a cancer in a subject in need thereof, comprising administering to the subject a combination of two or more agents selected from:
  (a) an epidermal growth factor receptor (EGFR) inhibitor;
  (b) a mitogen-activated protein kinase (MEK) 1/2 inhibitor; and
  (c) a cyclin dependent kinase (CDK) 4/6 inhibitor.

In certain embodiments, (a) is a small molecule or antibody (or antigen-binding fragment thereof) which specifically binds to EGFR or a ligand thereof, or is optionally selected from one or more of cetuximab, panitumumab, zalutumumab, nimotuzumab, matuzumab, erlotinib, gefitinib, afatinib, lapatinib, osimertinib, brigatinib, and icotinib.

In certain embodiments, (b) is a small molecule or antibody (or antigen-binding fragment thereof) which specifically binds to a MEK 1/2 or a ligand thereof, or is optionally selected from one or more of trametinib, selumetinib, and cobimetinib.

In certain embodiments, (c) is a small molecule or antibody (or antigen-binding fragment thereof) which specifically binds to a CDK 4/6 or a ligand thereof, or is optionally selected from one or more of palbociclib, ribociclib, and abemaciclib.

Some embodiments comprise administering the combination of (a) and (b) to the subject, optionally as separate compositions, or together as part of the same composition. Some embodiments comprise administering the combination of (a) and (c) to the subject, optionally as separate compositions, or together as part of the same composition. Some embodiments comprise administering the combination of (a), (b), and (c) to the subject, optionally as separate compositions, or together as part of the same composition.

In some embodiments, the cancer is a malignant epithelial tumor or carcinoma. In some embodiments, the carcinoma is selected from one or more of an adenocarcinoma, a squamous cell carcinoma, an adenosquamous carcinoma, an anaplastic carcinoma, a large cell carcinoma, and a small cell carcinoma. In some embodiments, the carcinoma is selected from one or more of an epithelial neoplasm, a squamous cell neoplasm (squamous cell carcinoma), a basal cell neoplasm (basal cell carcinoma), a transitional cell carcinoma, an adenocarcinoma (optionally a linitis plastica, a vipoma, a cholangiocarcinoma, a hepatocellular carcinoma, an adenoid cystic carcinoma, a renal cell carcinoma, or a Grawitz tumor), an adnexal or skin appendage neoplasm, a nucoepidermoid neoplasm, a cystic, mucinous, or Serous Neoplasm, a ductal, lobular, or medullary Neoplasm, an accinar cell neoplasm, and a complex epithelial neoplasm. In some embodiments, the cancer is a carcinoma selected from one or more of a colon cancer, a gastric cancer, a lung cancer (optionally small cell lung cancer or non-small lung cell cancer), a breast cancer, a pancreatic cancer, an oral cancer, a prostate cancer, a germline cancer, a rectal cancer, a liver cancer (optionally hepatocellular carcinoma), a kidney cancer (optionally renal cell carcinoma), and an ovarian cancer.

In some embodiments, the combination of (a) and (b) reduces cancer cell growth and/or increases cancer cell-killing by about or at least about 5, 10, 15, 20, 25, 30, 35, 40, 45, 50, 60, 70, 80, 90, 100, 200, 300, 400, 500, 600, 700, 800, 900, 1000, 2000% or more relative to (a) and/or (b) alone. In some embodiments, the combination of (a) and (b) synergistically reduces cancer cell growth and/or synergistically increases cancer cell-killing relative to (a) and/or (b) alone. In some embodiments, the combination of (a) and (c) reduces cancer cell growth and/or increases cancer cell-killing by about or at least about 5, 10, 15, 20, 25, 30, 35, 40, 45, 50, 60, 70, 80, 90, 100, 200, 300, 400, 500, 600, 700, 800, 900, 1000, 2000% or more relative to (a) and/or (c) alone. In some embodiments, the combination of (a) and (c) synergistically reduces cancer cell growth and/or synergistically increases cancer cell-killing relative to (a) and/or (c) alone. In some embodiments, the combination of (a), (b), and (c) reduces cancer cell growth by about or at least about 5, 10, 15, 20, 25, 30, 35, 40, 45, 50, 60, 70, 80, 90, 100, 200, 300, 400, 500, 600, 700, 800, 900, 1000, 2000% or more relative to (a), (b), and/or (c) alone. In some embodiments, the combination of (a), (b), and (c) synergistically reduces cancer cell growth and/or synergistically increases cancer cell-killing relative to (a), (b), and/or (c) alone.

In some embodiments, the combination of (a) and (b), (a) and (c), or (a), (b), and (c) is selected from a combination in Tables E1-E6, and optionally wherein the cancer corresponds to a cancer cell in Tables E1-E6.

Also included are therapeutic composition, comprising a combination of two or more agents selected from:
  (a) an epidermal growth factor receptor (EGFR) inhibitor;
  (b) a mitogen-activated protein kinase (MEK) 1/2 inhibitor; and
  (c) a cyclin dependent kinase (CDK) 4/6 inhibitor.

In some embodiments, (a) is a small molecule or antibody (or antigen-binding fragment thereof) which specifically binds to EGFR or a ligand thereof, and is optionally selected from one or more of cetuximab, panitumumab, zalutumumab, nimotuzumab, matuzumab, erlotinib, gefitinib, afatinib, lapatinib, osimertinib, brigatinib, and icotinib. In some embodiments, (b) is a small molecule or antibody (or antigen-binding fragment thereof) which specifically binds to a MEK 1/2 or a ligand thereof, and is optionally selected from one or more of trametinib, selumetinib, and cobimetinib. In some embodiments, (c) is a small molecule or antibody (or antigen-binding fragment thereof) which specifically binds to a CDK 4/6 or a ligand thereof, and is optionally selected from one or more of palbociclib, ribociclib, and abemaciclib.

Certain compositions comprise the combination of (a) and (b). Certain compositions comprise the combination of (a) and (c). Certain compositions comprise the combination of (a), (b), and (c).

In some embodiments, the combination of (a) and (b), (a) and (c), or (a), (b), and (c) is selected from a combination in Tables E1-E6, and optionally wherein the cancer corresponds to a cancer cell/tissue type in Tables E1-E6.

Certain therapeutic compositions are for use in treating a cancer in a subject in need thereof. In some embodiments, the cancer is a malignant epithelial tumor or carcinoma.

Also included are patient care kits, comprising a combination of two or more agents selected from:
  (a) an epidermal growth factor receptor (EGFR) inhibitor;
  (b) a mitogen-activated protein kinase (MEK) 1/2 inhibitor; and
  (c) a cyclin dependent kinase (CDK) 4/6 inhibitor.

Certain kits comprise the combination of (a) and (b), optionally as separate compositions or as part of the same composition. Some kits comprise the combination of (a) and (c), optionally as separate compositions or as part of the same composition. Certain kits comprise the combination of (a), (b), and (c), optionally as separate compositions or as part of the same composition.

BRIEF DESCRIPTION OF THE DRAWINGS

FIG. 1 shows images of patient-derived epithelial tumor cell following exposure to agents or combinations of agents.

DETAILED DESCRIPTION

Unless defined otherwise, all technical and scientific terms used herein have the same meaning as commonly understood by those of ordinary skill in the art to which the disclosure belongs. Although any methods, materials, compositions, reagents, cells, similar or equivalent similar or equivalent to those described herein can be used in the practice or testing of the subject matter of the present disclosure, preferred methods and materials are described. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes. As used herein, the term "antigen" includes substances that are capable, under appropriate conditions, of inducing an immune response to the substance and of reacting with the products of the immune response. For example, an antigen can be recognized by antibodies (humoral immune response) or sensitized T-lymphocytes (T helper or cell-mediated immune response), or both.

Antigens can be soluble substances, such as toxins and foreign proteins, or particulates, such as bacteria and tissue cells; however, only the portion of the protein or polysaccharide molecule known as the antigenic determinant (epitopes) combines with the antibody or a specific receptor on a lymphocyte. More broadly, the term "antigen" includes any substance to which an antibody binds, or for which antibodies are desired, regardless of whether the substance is immunogenic. For such antigens, antibodies can be identified by recombinant methods, independent of any immune response.

An "antagonist" or "inhibitor" refers to biological or chemical agent that interferes with or otherwise reduces the physiological action of another agent or molecule. In some instances, the antagonist specifically binds to the other agent or molecule. Included are full and partial antagonists and inhibitors.

An "agonist" refers to biological structure or chemical agent that increases or enhances the physiological action of another agent or molecule. In some instances, the agonist specifically binds to the other agent or molecule. Included are full and partial agonists.

As used herein, the term "amino acid" is intended to mean both naturally occurring and non-naturally occurring amino acids as well as amino acid analogs and mimetics. Naturally-occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

As used herein, a subject "at risk" of developing a disease, or adverse reaction may or may not have detectable disease, or symptoms of disease, and may or may not have displayed detectable disease or symptoms of disease prior to the treatment methods described herein. "At risk" denotes that a subject has one or more risk factors, which are measurable parameters that correlate with development of a disease, as described herein and known in the art. A subject having one or more of these risk factors has a higher probability of developing disease, or an adverse reaction than a subject without one or more of these risk factor(s).

"Biocompatible" refers to materials or compounds which are generally not injurious to biological functions of a cell or subject and which will not result in any degree of unacceptable toxicity, including allergenic and disease states.

The term "binding" refers to a direct association between two molecules, due to, for example, covalent, electrostatic, hydrophobic, and ionic and/or hydrogen-bond interactions, including interactions such as salt bridges and water bridges.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain micro-organisms, such as bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of active compound. Typically, 1 ng lipopolysaccharide (LPS) corresponds to about 1-10 EU.

The term "half maximal effective concentration" or "EC50" refers to the concentration of an agent (e.g., small molecule, antibody) as described herein at which it induces a response halfway between the baseline and maximum after some specified exposure time; the EC50 of a graded dose response curve therefore represents the concentration of a compound at which 50% of its maximal effect is observed. EC50 also represents the plasma concentration required for obtaining 50% of a maximum effect in vivo. Similarly, the "EC90" refers to the concentration of an agent or composition at which 90% of its maximal effect is observed. The "EC90" can be calculated from the "EC50" and the Hill slope, or it can be determined from the data directly, using routine knowledge in the art. In some embodiments, the EC50 of an agent (e.g., small molecule, antibody) is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, 100, 200 or 500 nM. In some embodiments, an agent will have an EC50 value of about InM or less.

The "half-life" of an agent can refer to the time it takes for the agent to lose half of its pharmacologic, physiologic, or other activity, relative to such activity at the time of administration into the serum or tissue of an organism, or relative to any other defined time-point. "Half-life" can also refer to the time it takes for the amount or concentration of an agent to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 1.5, 2, 3, 4, 5, 6, 7, 8, 9, 10, 15, 20, 30, 40, 50, 60, 70, 80, 90, 100 or more times (e.g., 500, 1000 times) (including all integers and ranges in between e.g., 1.5, 1.6, 1.7. 1.8, etc.) the amount produced by no composition (e.g., the absence of agent) or a control composition. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) in the amount produced by no composition (e.g., the absence of an agent) or a control composition. Examples of comparisons and "statistically significant" amounts are described herein.

The terms "polypeptide," "protein" and "peptide" are used interchangeably and mean a polymer of amino acids not limited to any particular length. The term "enzyme" includes polypeptide or protein catalysts. The terms include modifications such as myristoylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. In certain embodiments, the polypeptide is a "recombinant" polypeptide, produced by recombinant cell that comprises one or more recombinant DNA molecules, which are typically made of heterologous polynucleotide sequences or combinations of polynucleotide sequences that would not otherwise be found in the cell.

The term "isolated" polypeptide or protein referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or non-covalent interaction) with portions of a protein with which the "isolated protein" is associated in nature, (6) is operably associated (by covalent or non-covalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

In certain embodiments, the "purity" of any given agent (e.g., antibody, small molecule) in a composition may be defined. For instance, certain compositions may comprise an agent such as a polypeptide agent that is at least 80%, 85%, 90%, 91%, 92%, 93%, 94%, 95%, 96%, 97%, 98%, 99%, or 100% pure on a protein basis or a weight-weight basis, including all decimals and ranges in between, as measured, for example and by no means limiting, by high performance liquid chromatography (HPLC), a well-known form of column chromatography used frequently in biochemistry and analytical chemistry to separate, identify, and quantify compounds.

The term "solubility" refers to the property of an agent (e.g., antibody, small molecule) provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, pH 7.4, pH 7.6, pH 7.8, or pH 8.0 (e.g., about pH 5-8). In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90 or 100 mg/ml at room temperature or at 37° C.

A "subject" or a "subject in need thereof" or a "patient" or a "patient in need thereof" includes a mammalian subject such as a human subject.

"Substantially" or "essentially" means nearly totally or completely, for instance, 95%, 96%, 97%, 98%, 99% or greater of some given quantity.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Therapeutic response" refers to improvement of symptoms (whether or not sustained) based on administration of one or more therapeutic agents.

As used herein, the terms "therapeutically effective amount", "therapeutic dose," "prophylactically effective amount," or "diagnostically effective amount" is the amount of an agent (e.g., antibody, small molecule) needed to elicit the desired biological response following administration.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

The term "wild-type" refers to a gene or gene product (e.g., a polypeptide) that is most frequently observed in a population and is thus arbitrarily designed the "normal" or "wild-type" form of the gene.

Each embodiment in this specification is to be applied to every other embodiment unless expressly stated otherwise.

Pathways and Agents

Certain embodiments employ a combination of any two or more agents that inhibit or antagonize epidermal growth factor receptor (EGFR) activity, mitogen-activated protein kinase (MEK) 1/2 activity, and/or cyclin dependent kinase (CDK) 4/6 activity. General examples of such agents include small molecules and antibodies (or antigen binding fragments thereof), which are described in greater detail herein. EGFR.

The epidermal growth factor receptor (EGFR; ErbB-1; HER1 in humans) is a transmembrane protein that is a receptor for members of the epidermal growth factor family (EGF family) of extracellular protein ligands. EGF is a growth factor that stimulates cell growth, proliferation, and differentiation by binding to its receptor EGFR. Human EGF is a 6-kDa protein with 53 amino acid residues and three intramolecular disulfide bonds. EGF acts by binding with high affinity to EGFR on the cell surface. This stimulates ligand-induced dimerization, which activates the intrinsic protein-tyrosine kinase activity of the receptor. The tyrosine kinase activity then initiates a signal transduction cascade that results in a variety of biochemical changes within the cell, including a rise in intracellular calcium levels, increased glycolysis and protein synthesis, and increased expression of certain genes, including those involved in DNA synthesis and cell proliferation.

Mutations that lead to EGFR overexpression or over activity are associated with a variety of cancers, including squamous-cell carcinoma of the lung, anal cancers, glioblastoma, and epithelial tumors of the head and neck, among others. Thus, in certain embodiments, the agent inhibits an EGFR activity or an EGFR-regulated pathway.

For example, in certain embodiments the agent is an antibody (or antigen-binding fragment thereof) that specifically binds to EGFR, for example, which specifically binds to the extracellular ligand binding domain of EGFR and optionally inhibits or reduces the binding of stimulatory ligands or signal molecules such as EGF. Illustrative anti-EGFR antibodies are described, for example, in U.S. Pat. Nos. 5,844,093; 7,132,511; 7,247,301; 7,595,378; 7,723,484; 7,939,072; and 7,960,516, which are incorporated by reference. Specific non-limiting examples of EGFR inhibitor antibodies include cetuximab, panitumumab, zalutumumab, nimotuzumab, and matuzumab, and fragments or variants thereof. In specific embodiments, the antibody is cetuximab (Erbitux®), or a fragment or variant thereof. Cetuximab is composed of the Fv (variable; antigen-binding) regions of the 225 murine EGFR monoclonal antibody specific for the N-terminal portion of human EGFR with human IgG1 heavy and kappa light chain constant (framework) regions.

Also included are small molecule inhibitors of EGFR, for example, tyrosine kinase inhibitors of EGFR kinase activity. Non-limiting examples of small molecule EGFR inhibitors include erlotinib, gefitinib, afatinib, lapatinib, osimertinib, brigatinib, and icotinib. Thus, in certain embodiments, the EGFR inhibitor is any one or more of the foregoing antibodies or small molecules.

MEK 1/2.

Mitogen-activated protein kinase (MAPK) cascades are key signaling pathways involved in the regulation of normal cell proliferation, survival, and differentiation. Aberrant regulation of MAPK cascades contribute to cancer and other human diseases. In particular, the extracellular signal-regulated kinase (ERK) MAPK pathway has been implicated in many cancers as a therapeutic target. ERK is a downstream component of an evolutionarily conserved signaling module that is activated by the Raf serine/threonine kinases. Raf activates the MAPK/ERK kinase (MEK) 1/2 dual-specificity protein kinases, which then activate ERK1/2. The mutational activation of Raf in human cancers supports the important role of this pathway in human oncogenesis. Additionally, the Raf-MEK-ERK pathway is a key downstream effector of the Ras small GTPase, the most frequently mutated oncogene in human cancers. Lastly, Ras is a key downstream effector of the epidermal growth factor receptor (EGFR), which is mutationally activated and/or overexpressed in a wide variety of human cancers. ERK activation also promotes upregulated expression of EGFR ligands, promoting an autocrine growth loop critical for tumor growth.

Thus, certain embodiments are directed to modulating (e.g., inhibiting) the EGFR-Ras-Raf-MEK-ERK signaling pathway, for example, by inhibiting the MEK 1/2 dual-specificity protein kinases. Some embodiments therefore include small molecules that inhibit MEK1 and/or MEK2. Non-limiting examples of small molecule MEK 1/2 inhibitors include trametinib, selumetinib, cobimetinib, and binimetinib. Additional examples of MEK1 and MEK2 inhibitors are described, for example, in U.S. Application No. 2009/0124595; U.S. Application No. 2009/0246198; and U.S. Application No. 2010/0004234, which are incorporated by reference.

CDK 4/6.

Cyclin-dependent kinases (CDKs) are a family of protein kinases that play a role in regulating the cell cycle. CDK4 and CDK6 regulate the cell G1 phase progression and the G1/S transition of the cell cycle. CDK4 and CDK6 have been shown to phosphorylate and thus regulate the activity of the tumor suppressor Retinoblastoma protein, and are overexpressed or otherwise unbalanced in a variety of tumors. For example, the overexpression of CDK4 and CDK6 can provide cancer cells certain hallmarks of cancer, including deregulation of the cell cycle and of cell metabolism.

Thus, certain embodiments are directed to modulating (e.g., inhibiting) CDK 4/6-regulated pathways, for example, by inhibiting the CDK4 and/or CDK6 kinases. Included are agents that inhibit the ability or activity of CDK 4/6 to phosphorylate a serine or threonine residue on proteins, or inhibit the interaction of CDK 4/6 with other proteins/ligands that are involved in the signal pathway. CDK4 and CDK6 form a complex with Cyclin D to regulate cell cycle progression from G1 to S phase. CDK4 has been shown to interact with retinoblastoma (Rb), CDC37, CDKN1B, CDKN2B, CDKN2C, CEBPA, CCND1, CCND3, DBNL, MyoD, P16, PCNA, and SERTAD1. CDK6 has been shown to interact with retinoblastoma (RB), CDKN2C, PPM1B, Cyclin D3, Cyclin D1, and PPP2CA. Thus, in certain embodiments, the CDK 4/6 inhibitor reduces the interaction of CDK4 and/or CDK6 with any one or more of the foregoing proteins or ligands.

Some embodiments therefore include small molecules that inhibit CDK4 and/or CDK6. Non-limiting examples of small molecule CDK 4/6 inhibitors include ribociclib, abemaciclib, and palbociclib. Additional examples of CDK 4/6 inhibitors are described, for example, in WO 2007/140222; WO 2010/020675; and U.S. Application No. 2013/0035336, which are incorporated by reference.

Antibodies.

In some embodiments, as noted above, the agent is an antibody or "antigen-binding fragment thereof." The antibody or antigen-binding fragment can be of essentially any type. As is well known in the art, an antibody is an immunoglobulin molecule capable of specific binding to a target through at least one epitope recognition site, located in the variable region of the immunoglobulin molecule. In certain embodiments, the target is EGFR (e.g., the ligand binding domain of EGFR), EGR, MEK1, MEK2, CDK4, CDK6, or any combination thereof, or any ligand thereof. Thus, in certain embodiments, an antibody specifically binds to a target described herein with a binding affinity (Kd) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In certain embodiments, an antibody (or antigen-binding fragment thereof) specifically binds to and/or inhibits EGFR, MEK1, MEK2, CDK4, CDK6, or any combination thereof, including any ligand thereof (e.g., EGR), as described herein and known in the art.

As used herein, the term "antibody" encompasses not only intact polyclonal or monoclonal antibodies, but also fragments thereof (such as dAb, Fab, Fab', F(ab')2, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. Certain features and characteristics of antibodies (and antigen-binding fragments thereof) are described in greater detail herein.

The term "antigen-binding fragment" as used herein refers to a polypeptide fragment that contains at least one CDR of an immunoglobulin heavy and/or light chain that binds to the antigen of interest. In this regard, an antigen-binding fragment of the herein described antibodies may comprise 1, 2, 3, 4, 5, or all 6 CDRs of a VH and VL sequence from antibodies that bind to a target molecule.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. Epitopes can be contiguous or non-contiguous in relation to the primary structure of the antigen.

A molecule such as an antibody is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances, for example, by a statistically significant amount. For instance, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant (Kd) of the interaction, wherein a smaller Kd represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" (Kon) and the "off rate constant" (Koff) can be determined by calculation of the concentrations and actual rates of association and dissociation. The ratio of Koff/Kon enables cancellation of all parameters not related to affinity, and is thus equal to the dissociation constant Kd.

Antibodies may be prepared by any of a variety of techniques known to those of ordinary skill in the art. See, e.g., Harlow and Lane, Antibodies: A Laboratory Manual, Cold Spring Harbor Laboratory, 1988. Monoclonal antibodies specific for a polypeptide of interest may be prepared, for example, using the technique of Kohler and Milstein, Eur. J. Immunol. 6:511-519, 1976, and improvements thereto. Also included are methods that utilize transgenic animals such as mice to express human antibodies. See, e.g., Neuberger et al., Nature Biotechnology 14:826, 1996; Lonberg et al., Handbook of Experimental Pharmacology 113:49-101, 1994; and Lonberg et al., Internal Review of Immunology 13:65-93, 1995. Particular examples include the VELOCIMMUNE® platform by REGENEREX® (see, e.g., U.S. Pat. No. 6,596,541).

Antibodies can also be generated or identified by the use of phage display or yeast display libraries (see, e.g., U.S. Pat. No. 7,244,592; Chao et al., Nature Protocols. 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures-regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

Also include are "monoclonal" antibodies, which refer to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')2, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments etc. described above under the definition of "antibody."

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent VH::VL heterodimer including an antigen-binding site which retains much of the antigen recognition and binding capabilities of the native antibody molecule. See Inbar et al., PNAS USA. 69:2659-2662, 1972; Hochman et al., Biochem. 15:2706-2710, 1976; and Ehrlich et al., Biochem. 19:4091-4096, 1980.

In certain embodiments, single chain Fv or scFV antibodies are contemplated. For example, Kappa bodies (Ill et al., Prot. Eng. 10:949-57, 1997); minibodies (Martin et al., EMBO J 13:5305-9, 1994); diabodies (Holliger et al., PNAS 90: 6444-8, 1993); or Janusins (Traunecker et al., EMBO J 10: 3655-59, 1991; and Traunecker et al., Int. J. Cancer Suppl. 7:51-52, 1992), may be prepared using standard molecular biology techniques following the teachings of the present application with regard to selecting antibodies having the desired specificity.

A single chain Fv (sFv) polypeptide is a covalently linked VH::VL heterodimer which is expressed from a gene fusion including VH- and VL-encoding genes linked by a peptide-encoding linker. Huston et al. (PNAS USA. 85(16):5879-5883, 1988). A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, an antibody as described herein is in the form of a "diabody." Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804). A dAb fragment of an antibody consists of a VH domain (Ward et al., Nature 341:544-546, 1989). Diabodies and other multivalent or multispecific fragments can be constructed, for example, by gene fusion (see WO94/13804; and Holliger et al., PNAS USA. 90:6444-6448, 1993)).

Minibodies comprising a scFv joined to a CH3 domain are also included (see Hu et al., Cancer Res. 56:3055-3061, 1996). See also Ward et al., Nature. 341:544-546, 1989; Bird et al., Science. 242:423-426, 1988; Huston et al., PNAS USA. 85:5879-5883, 1988); PCT/US92/09965; WO94/13804; and Reiter et al., Nature Biotech. 14:1239-1245, 1996.

Where bispecific antibodies are to be used, these may be conventional bispecific antibodies, which can be manufactured in a variety of ways (Holliger and Winter, Current Opinion Biotechnol. 4:446-449, 1993), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (Ridgeway et al., Protein Eng., 9:616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies provided herein may take the form of a nanobody. Minibodies are encoded by single genes and are efficiently produced in almost all prokaryotic and eukaryotic hosts, for example, *E. coli* (see U.S. Pat. No. 6,765,087), molds (for example *Aspergillus* or *Trichoderma*) and yeast (for example *Saccharomyces, Kluyvermyces, Hansenula* or *Pichia* (see U.S. Pat. No. 6,838,254). The production process is scalable and multi-kilogram quantities of nanobodies have been produced. Nanobodies may be formulated as a ready-to-use solution having a long shelf life. The Nanoclone method (see WO 06/079372) is a proprietary method for generating Nanobodies against a desired target, based on automated high-throughput selection of B-cells.

In certain embodiments, the antibodies or antigen-binding fragments thereof are humanized. These embodiments refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio et al., PNAS USA 86:4220-4224, 1989; Queen et al., PNAS USA. 86:10029-10033, 1988; Riechmann et al., Nature. 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato et al., Cancer Res. 53:851-856, 1993; Riechmann et al., Nature 332:323-327, 1988; Verhoeyen et al., Science 239:1534-1536, 1988; Kettleborough et al., Protein Engineering. 4:773-3783, 1991; Maeda et al., Human Antibodies Hybridoma 2:124-134, 1991; Gorman et al., PNAS USA. 88:4181-4185, 1991; Tempest et al., Bio/Technology 9:266-271, 1991; Co et al., PNAS USA. 88:2869-2873, 1991; Carter et al., PNAS USA. 89:4285-4289, 1992; and Co et al., J Immunol. 148:1149-1154, 1992. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies may be chimeric antibodies. In this regard, a chimeric antibody is comprised of an antigen-binding fragment of an antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

Small Molecules.

In particular embodiments, the inhibitor or antagonist is a "small molecule". A small molecule refers to an organic compound that is of synthetic or biological origin (biomolecule), but which is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of less than about 1000-2000 Daltons, typically between about 300 and 700 Daltons, and including about 50, 100, 150, 200, 250, 300, 350, 400, 450, 500, 550, 500, 650, 600, 750, 700, 850, 800, 950, 1000 or 2000 Daltons.

Certain small molecules can have the "specific binding" characteristics described for antibodies. For instance, in some embodiments, a small molecule specifically binds to a target described herein with a binding affinity (Kd) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In certain embodiments, a small molecule specifically binds to and/or inhibits EGFR, MEK1, MEK2, CDK4, CDK6, or any combination thereof, including any ligand thereof (e.g., EGR), as described herein and known in the art.

Methods of Use and Therapeutic Compositions

As noted above, embodiments of the present disclosure relate to the discovery that certain combinations of at least two agents provide significant and often synergistically increased cancer cell growth inhibition activity in an ex vivo model of primary cell cancer, relative to the individual agents alone. Some embodiments therefore relate to methods of treating, ameliorating the symptoms of, or inhibiting the progression of, a cancer in a subject in need thereof, comprising administering to the subject a combination of two or more agents selected from an epidermal growth factor receptor (EGFR) inhibitor, a mitogen-activated protein kinase (MEK) 1/2 inhibitor, and a cyclin dependent kinase (CDK) 4/6 inhibitor. Particular examples of the foregoing agents are described herein.

Certain methods include administering a combination of an EGFR inhibitor and a MEK 1/2 inhibitor. Some methods include administering a combination of an EGFR inhibitor and a CDK 4/6 inhibitor. Particular methods include administering a combination of a MEK 1/2 inhibitor and a CDK 4/6 inhibitor. Certain methods include administering a combination of an EGFR inhibitor, a MEK 1/2 inhibitor, and a CDK 4/6 inhibitor. In some instances, the agents are administered separately, for example, in separate therapeutic compositions and at the same or different times. In some embodiments, the agents are administered as part of the same therapeutic composition, at the same time.

In some embodiments, the combination of agents reduces cancer cell growth and/or increases cancer cell-killing by about or at least about 5, 10, 15, 20, 25, 30, 35, 40, 45, 50, 60, 70, 80, 90, 100, 200, 300, 400, 500, 600, 700, 800, 900, 1000, 2000% or more relative to each individual agent alone. In some embodiments, the combination of agents synergistically reduces cancer cell growth and/or synergistically increases cancer cell-killing relative to each individual agent alone.

In some embodiments, the methods and therapeutic compositions described herein increase median survival time of a subject by at least 4 weeks, 5 weeks, 6 weeks, 7 weeks, 8 weeks, 9 weeks, 10 weeks, 15 weeks, 20 weeks, 25 weeks, 30 weeks, 40 weeks, 50 weeks, 60 weeks, 70 weeks, 80 weeks, 90 weeks, 100 weeks, or longer. In certain embodiments, the methods and therapeutic compositions described herein increase median survival time of a subject by at least 1 year, 2 years, 3 years, 4 years, 5 years, or longer. In some embodiments, the methods and therapeutic compositions described herein increase progression-free survival by 2 weeks, 3 weeks, 4 weeks, 5 weeks, 6 weeks, 7 weeks, 8 weeks, 9 weeks, 10 weeks, 15 weeks, 20 weeks, 25 weeks, 30 weeks, 40 weeks, 50 weeks, 60 weeks, 70 weeks, 80 weeks, 90 weeks, 100 weeks, or longer. In certain embodiments, the methods or therapeutic compositions described herein increase progression-free survival by 1 year, 2 years, 3 years, 4 years, 5 years, or longer.

In certain embodiments, the methods and therapeutic compositions described herein are sufficient to result in tumor regression, as indicated by a statistically significant decrease in the amount of viable tumor, for example, at least a 10%, 20%, 30%, 40%, 50%, 60%, 70%, 80%, 90%, 100% or greater decrease in tumor mass, or by altered (e.g., decreased with statistical significance) scan dimensions. In certain embodiments, the methods and therapeutic compositions described herein are sufficient to result in stable disease. In certain embodiments, the methods and therapeutic compositions described herein are sufficient to result in clinically relevant reduction in symptoms of a particular disease indication known to the skilled clinician.

In some embodiments, the combination of agents is selected from a combination provided in Tables E1-E6.

The methods and therapeutic compositions described herein can be used in the treatment of any variety of cancers. In some embodiments, the cancer is a malignant epithelial tumor or carcinoma. In some embodiments, the carcinoma is selected from one or more of an epithelial neoplasm, a squamous cell neoplasm (squamous cell carcinoma), a basal cell neoplasm (basal cell carcinoma), a transitional cell carcinoma, an adenocarcinoma (optionally a linitis plastica, a vipoma, a cholangiocarcinoma, a hepatocellular carcinoma, an adenoid cystic carcinoma, a renal cell carcinoma, or a Grawitz tumor), an adnexal or skin appendage neoplasm, a nucoepidermoid neoplasm, a cystic, mucinous, or Serous Neoplasm, a ductal, lobular, or medullary Neoplasm, an accinar cell neoplasm, and a complex epithelial neoplasm.

In some embodiments, the cancer or carcinoma is selected from one or more of a colon or colorectal cancer, a gastric cancer, a lung cancer (optionally small cell lung cancer or non-small lung cell cancer), a breast cancer (for example, estrogen receptor positive (ER+), estrogen receptor negative (ER−), Her2 positive (Her2+), Her2 negative (Her2−), or a combination thereof, e.g., ER+/Her2+, ER+/Her2−, ER−/Her2+, or ER−/Her2−; or "triple negative" breast cancer which is estrogen receptor-negative, progesterone receptor-negative, and HER2-negative), a pancreatic cancer, an oral cancer, a prostate cancer, a germline cancer, a rectal cancer, a liver cancer (optionally hepatocellular carcinoma), a kidney cancer (optionally renal cell carcinoma), and an ovarian cancer. In some embodiments, the cancer or carcinoma is metastatic cancer of any one of the foregoing.

In some embodiments, the cancer or carcinoma is selected from one or more of melanoma (e.g., metastatic melanoma), bone cancer, mesothelioma, leukemia (e.g., lymphocytic leukemia, chronic myelogenous leukemia, acute myeloid leukemia, relapsed acute myeloid leukemia), lymphoma, sarcoma, B-cell malignancy, glioma (e.g., astrocytoma, oligodendroglioma, ependymoma, or a choroid plexus papilloma), glioblastoma multiforme (e.g., giant cell gliobastoma or a gliosarcoma), meningioma, pituitary adenoma, vestibular schwannoma, primary CNS lymphoma, primitive neuroectodermal tumor (medulloblastoma), bladder cancer, uterine cancer, esophageal cancer, laryngeal cancer, brain cancer, head and neck cancers, cervical cancer, testicular cancer, stomach cancer, virus-induced tumors such as, for example, papilloma virus-induced carcinomas (e.g., cervical carcinoma, cervical cancer), adenocarcinomas, herpes virus-induced tumors (e.g. Burkitt's lymphoma, EBV-induced B-cell lymphoma), hepatitis B-induced tumors (hepatocellular carcinomas), HTLV-1-indued and HTLV-2-induced lymphomas, acoustic neuroma, lung cancers (e.g., lung carcinoma, bronchial carcinoma), pharyngeal cancer, anal carcinoma, glioblastoma, rectal carcinoma, astrocytoma, brain tumors, retinoblastoma, basalioma, brain metastases, medulloblastomas, vaginal cancer, Hodgkin's syndrome, meningiomas, Schneeberger disease, hypophysis tumor, Mycosis fungoides, carcinoids, neurinoma, spinalioma, Burkitt's lymphoma, renal cancer, thymoma, corpus carcinoma, bone cancer, non-Hodgkin's lymphomas, urethral cancer, CUP syndrome, head/neck tumors, oligodendroglioma, vulval cancer, intestinal cancer, oesophageal cancer, wart involvement, tumors of the small intestine, craniopharyngeomas, genital tumors, endometrial carcinoma, liver metastases, penile cancer, tongue cancer, gall bladder cancer, plasmocytoma, and lid tumor. In some embodiments, the cancer or carcinoma is a metastatic cancer of any one of the foregoing.

In some embodiments, the cancer or carcinoma has an EGFR-associated mutation or alteration, and at least one of the agents is an EGFR inhibitor. Examples include an EGFR-expressing or overexpressing cancer or carcinoma. In some embodiments, the cancer has an EGFR mutation, for example, an EGFR exon 19 deletion and/or an exon 21 L858R substitution mutation.

In some embodiments, the cancer or carcinoma type is selected from Tables E1-E6, and is optionally treated by the corresponding combination of agents provided in Tables E1-E6.

The methods for treating cancers can be combined with other therapeutic modalities. For example, a combination therapy described herein can be administered to a subject before, during, or after other therapeutic interventions, including symptomatic care, radiotherapy, surgery, transplantation, hormone therapy, photodynamic therapy, antibiotic therapy, or any combination thereof. Symptomatic care includes administration of corticosteroids, to reduce cerebral edema, headaches, cognitive dysfunction, and emesis, and administration of anti-convulsants, to reduce seizures. Radiotherapy includes whole-brain irradiation, fractionated radiotherapy, and radiosurgery, such as stereotactic radiosurgery, which can be further combined with traditional surgery.

Methods for identifying subjects with one or more of the diseases or conditions described herein are known in the art.

For in vivo use, as noted above, for the treatment of human disease or testing, the agents described herein are generally incorporated into one or more therapeutic or pharmaceutical compositions prior to administration.

Thus, certain embodiments relate to therapeutic compositions that comprise a combination of two or more (e.g., 3, 4, 5, 6) agents selected from an EGFR inhibitor, a MEK 1/2 inhibitor, and a CDK 4/6 inhibitor, as described herein. Some therapeutic compositions comprise the combination of an EGFR inhibitor and a MEK 1/2 inhibitor. Certain therapeutic compositions comprise the combination of an EGFR inhibitor and a CDK 4/6 inhibitor. Particular therapeutic compositions comprise the combination of a MEK 1/2 inhibitor and a CDK 4/6 inhibitor. Some therapeutic compositions comprise the combination of an EGFR inhibitor, a MEK 1/2 inhibitor, and a CDK 4/6 inhibitor. In particular embodiments, the therapeutic composition comprises combination of agents selected from a combination provided in Tables E1-E6.

In some instances, a therapeutic or pharmaceutical composition comprises one or more of the agents described herein in combination with a pharmaceutically- or physiologically-acceptable carrier or excipient. Certain therapeutic compositions further comprise at least one cancer immunotherapy agent, as described herein.

In particular embodiments, the therapeutic composition comprising the agents such as antibodies is substantially pure on a protein basis or a weight-weight basis, for example, the composition has a purity of at least about 80%, 85%, 90%, 95%, 98%, or 99% on a protein basis or a weight-weight basis.

In some embodiments, the antibodies provided herein do not form aggregates, have a desired solubility, and/or have an immunogenicity profile that is suitable for use in humans, as described herein and known in the art. Thus, in some embodiments, the therapeutic composition comprising an antibody agent is substantially aggregate-free. For example, certain compositions comprise less than about 10% (on a protein basis) high molecular weight aggregated proteins, or less than about 5% high molecular weight aggregated proteins, or less than about 4% high molecular weight aggregated proteins, or less than about 3% high molecular weight aggregated proteins, or less than about 2% high molecular weight aggregated proteins, or less than about 1% high molecular weight aggregated proteins. Some compositions comprise an antibody agent that is at least about 50%, about 60%, about 70%, about 80%, about 90% or about 95% monodisperse with respect to its apparent molecular mass.

In some embodiments, antibody agents are concentrated to about or at least about 0.1 mg/ml, 0.2 mg/ml, 0.3 mg/ml, 0.4 mg/ml, 0.5 mg/ml, 0.6, 0.7, 0.8, 0.9, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11, 12, 13, 14 or 15 mg/ml and are formulated for biotherapeutic uses.

To prepare a therapeutic or pharmaceutical composition, an effective or desired amount of one or more agents is mixed with any pharmaceutical carrier(s) or excipient known to those skilled in the art to be suitable for the particular agent and/or mode of administration. A pharmaceutical carrier may be liquid, semi-liquid or solid. Solutions or suspensions used for parenteral, intradermal, subcutaneous or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously (e.g., by IV infusion), suitable carriers include physiological saline or phosphate buffered saline (PBS), and solutions containing thickening and solubilizing agents, such as glucose, polyethylene glycol, polypropylene glycol and mixtures thereof.

Administration of agents described herein, in pure form or in an appropriate therapeutic or pharmaceutical composition, can be carried out via any of the accepted modes of administration of agents for serving similar utilities. The therapeutic or pharmaceutical compositions can be prepared by combining an agent-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other small molecules as described elsewhere herein) and/or suitable excipients such as salts, buffers and stabilizers may, but need not, be present within the composition.

Administration may be achieved by a variety of different routes, including oral, parenteral, nasal, intravenous, intradermal, intramuscular, subcutaneous or topical. Preferred modes of administration depend upon the nature of the condition to be treated or prevented. Particular embodiments include administration by IV infusion.

Carriers can include, for example, pharmaceutically- or physiologically-acceptable carriers, excipients, or stabilizers that are non-toxic to the cell or mammal being exposed thereto at the dosages and concentrations employed. Often the physiologically-acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, one or more agents can be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Typical routes of administering these and related therapeutic or pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Therapeutic or pharmaceutical compositions according to certain embodiments of the present disclosure are formulated so as to allow the active ingredients contained therein to be bioavailable upon administration of the composition to a subject or patient. Compositions that will be administered to a subject or patient may take the form of one or more dosage units, where for example, a tablet may be a single dosage unit, and a container of a herein described agent in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will typically contain a therapeutically effective amount of an agent described herein, for treatment of a disease or condition of interest.

A therapeutic or pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid. Certain embodiments include sterile, injectable solutions.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The therapeutic or pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid therapeutic or pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid therapeutic or pharmaceutical composition intended for either parenteral or oral administration should contain an amount of an agent such that a suitable dosage will be obtained. Typically, this amount is at least 0.01% of the agent of interest in the composition. When intended for oral administration, this amount may be varied to be between 0.1 and about 70% of the weight of the composition. Certain oral therapeutic or pharmaceutical compositions contain between about 4% and about 75% of the agent of interest. In certain embodiments, therapeutic or pharmaceutical compositions and preparations according to the present invention are prepared so that a parenteral dosage unit contains between 0.01 to 10% by weight of the agent of interest prior to dilution.

The therapeutic or pharmaceutical compositions may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a therapeutic or pharmaceutical composition for topical administration. If intended for transdermal administration, the composition may include a transdermal patch or iontophoresis device.

The therapeutic or pharmaceutical compositions may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The therapeutic or pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The therapeutic or pharmaceutical compositions in solid or liquid form may include a component that binds to agent and thereby assists in the delivery of the compound. Suitable components that may act in this capacity include monoclonal or polyclonal antibodies, one or more proteins or a liposome.

The therapeutic or pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions described herein may be prepared with carriers that protect the agents against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The therapeutic or pharmaceutical compositions may be prepared by methodology well known in the pharmaceutical art. For example, a therapeutic or pharmaceutical composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the agent so as to facilitate dissolution or homogeneous suspension of the agent in the aqueous delivery system.

The combination therapies described herein may include administration of a single pharmaceutical dosage formulation, which contains a combination of two or three or more agents (optionally with one or more additional active agents), as well as administration of compositions comprising each individual agent in its own separate pharmaceutical dosage formulation. For example, an EGFR inhibitor and a MEK 1/2 inhibitor can be administered to the subject together in a single oral dosage composition such as a tablet or capsule, or each agent administered in separate oral dosage formulations. Similarly, an EGFR inhibitor and a MEK 1/2 inhibitor can be administered to the subject together in a single parenteral dosage composition such as in a saline solution or other physiologically acceptable solution, or each agent administered in separate parenteral dosage formulations. Likewise, an EGFR inhibitor and a CDK 4/6 inhibitor can be administered to the subject together in a single oral dosage composition such as a tablet or capsule, or each agent administered in separate oral dosage formulations. Also, an EGFR inhibitor and a CDK 4/6 inhibitor can be administered to the subject together in a single parenteral dosage composition such as in a saline solution or other physiologically acceptable solution, or each agent administered in separate parenteral dosage formulations. As another example, a MEK 1/2 and a CDK 4/6 inhibitor can be administered to the subject together in a single oral dosage composition such as a tablet or capsule, or each agent administered in separate oral dosage formulations. Likewise, a MEK 1/2 inhibitor and a CDK 4/6 inhibitor can be administered to the subject together in a single parenteral dosage composition such as in a saline solution or other physiologically acceptable solution, or each agent administered in separate parenteral dosage formulations. As a further example, an EGFR inhibitor, a MEK 1/2, and a CDK 4/6 inhibitor can be administered to the subject together in a single oral dosage composition such as a tablet or capsule, or each agent administered in separate oral dosage formulations. Similarly, an EGFR inhibitor, a MEK 1/2 inhibitor, and a CDK 4/6 inhibitor can be administered to the subject together in a single parenteral dosage composition such as in a saline solution or other physiologically acceptable solution, or each agent administered in separate parenteral dosage formulations. Where separate dosage formulations are used, the compositions can be administered at essentially the same time, i.e., concurrently, or at separately staggered times, i.e., sequentially and in any order; combination therapy is understood to include all these regimens.

Also included are patient care kits, comprising a combination of two or more (e.g., 3, 4, 5, 6) agents selected from an EGFR inhibitor, a MEK 1/2 inhibitor, and a CDK 4/6 inhibitor. Some patient care kits comprise the combination of an EGFR inhibitor and a MEK 1/2 inhibitor, optionally as separate compositions or as part of the same composition. Certain patient care kits comprise the combination of an EGFR inhibitor and a CDK 4/6 inhibitor, optionally as separate compositions or as part of the same composition. Certain patient care kits comprise the combination of a MEK 1/2 inhibitor and a CDK 4/6 inhibitor, optionally as separate compositions or as part of the same composition. Particular patient care kits comprise the combination of an EGFR inhibitor, a MEK 1/2 inhibitor, and a CDK 4/6 inhibitor, optionally as separate compositions or as part of the same composition. In particular embodiments, the patient care kit comprises combination of agents selected from a combination provided in Tables E1-E6, optionally as separate compositions or as part of the same composition.

The kits herein may also include a one or more additional therapeutic agents or other components suitable or desired for the indication being treated, or for the desired diagnostic application. The kits herein can also include one or more syringes or other components necessary or desired to facilitate an intended mode of delivery (e.g., stents, implantable depots, etc.).

In some embodiments, a patient care kit contains separate containers, dividers, or compartments for the composition(s) and informational material(s). For example, the composition(s) can be contained in a bottle, vial, or syringe, and the informational material(s) can be contained in association with the container. In some embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an agent or agents described herein. For example, the kit includes a plurality of syringes, ampules, foil packets, or blister packs, each containing a single unit dose of each agent. The containers of the kits can be air tight, waterproof (e.g., impermeable to changes in moisture or evaporation), and/or light-tight.

The patient care kit optionally includes a device suitable for administration of the composition, e.g., a syringe, inhalant, dropper (e.g., eye dropper), swab (e.g., a cotton swab or wooden swab), or any such delivery device. In some embodiments, the device is an implantable device that dispenses metered doses of the agent(s). Also included are methods of providing a kit, e.g., by combining the components described herein.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Ex Vivo Drug Tests Using Conditional Reprogramming Cell Pools

Surgical specimen from colorectal cancer patients, liver cancer patients, lung cancer patients, pancreatic cancer, gastric cancer patients and breast cancer patients were obtained from the Beijing Cancer Hospital and the Cancer Hospital of Chinese Academy of Medical Science after receiving patient consensus. Patient-derived xenograft tumor specimens were obtained from Nod/SCID mice inoculated with surgical tumor specimen from patients.

For ex vivo drug sensitivity assays, the tumor cells were isolated from the patient tissue sample or PDX xenograft tumor tissue. Briefly, the tumor tissues were cut into small pieces less than 1 mm in diameter using scissors. The tumor fragments were transferred into a sterile 100-ml triangle glass flask loaded with a magnet stir bar. A 10-15 ml digestion media containing 0.25 U/ml Liberase DH was added into the minced tumor tissues to start enzyme digestion. The enzyme mixture was incubated at 37° C. for 1-2 hours with moderate stirring. The digested tumor tissue was filtered through a 100-µm cell retainer. The filtrates were re-filtered through a 40-µm cell restrainer. The tumor cell clusters retained on the 40-µm cell restrainer was collected, wash twice with HBSS, then re-suspended in a defined growth media supplemented with several stem cell growth factors.

The tumor cell clusters retained on the 40-µm cell restrainer were collected, wash twice with HBSS, then re-suspended in a defined growth media supplemented with cell growth factors and small molecule inhibitors. The tumor cell clusters were recovered in a defined growth medium overnight. The defined growth medium was StemPro® hESC SFM (defined, serum- and feeder-free medium (SFM)) supplemented with: Nicotinamide, Wnt3A, Noggin (Bone Morphogenetic Protein (BMP) inhibitor), R-spondin-1 (Wnt/β-catenin signaling agonist), and Y27632 (Rho-associated, coiled-coil containing protein kinase (ROCK-1) inhibitor).

For conditional reprogramming, the recovered CTOSs were dissociated into single cells and seeded in a feeder cell/Rock inhibitor (Y27632) co-culture system at about 3000 cells per well in cell culture plate, and grow at 37 C for 3 days.

For ex vivo drug testing, the seeded tumor cells were exposed to seven EGFR inhibitors, three MEK 1/2 inhibitors, and three CDK 4/6 inhibitors alone, or a combination of EGFR inhibitor and MEK 1/2 inhibitor, a combination of EGFR inhibitor and CDK 4/6 inhibitor, a combination of MEK 1/2 inhibitor and CDK 4/6 inhibitor, and a triple combination of EGFR inhibitor, MEK 1/2 inhibitor, and a CDK 4/6 inhibitor for 72 hours. The treated tumor cells were re-exposed to the same drug or drug combination with a fresh media change for another 72 hours. All drugs were prepared in DMSO and the final concentration of DMSO in media was 0.1%. The tested concentration of the drug and drug combinations were at relevant AUC concentration (see Table E1).

TABLE E1

| control DMSO 0.2% | control DMSO 0.5% | Erlotinib 5 | Erlotinib 1 | Afatinib 0.2 | Afatinib 0.04 |
|---|---|---|---|---|---|
| Dabrafenib 2 | Dabrafenib 0.4 | Erlotinib + Dabrafenib 5 + 2 | Erlotinib + Dabrafenib 1 + 0.4 | Afatinib + Dabrafenib 0.2 + 2 | Afatinib + Dabrafenib 0.04 + 0.4 |
| Trametinib 0.02 | Trametinib 0.004 | Erlotinib + Trametinib 5 + 0.02 | Erlotinib + Trametinib 1 + 0.004 | Afatinib + Trametinib 0.2 + 0.02 | Afatinib + Trametinib 0.04 + 0.004 |
| Palbociclib 0.5 | Palbociclib 0.1 | Erlotinib + Palbociclib 5 + 0.5 | Erlotinib + Palbociclib 1 + 0.1 | Afatinib + Palbociclib 0.2 + 0.5 | Afatinib + Palbociclib 0.04 + 0.1 |
| Dabrafenib + Trametinib 2 + 0.02 | Dabrafenib + Trametinib 0.4 + 0.004 | Erlotinib + Dabrafenib + Trametinib 5 + 2 + 0.02 | Erlotinib + Dabrafenib + Trametinib 1 + 0.4 + 0.004 | Afatinib + Dabrafenib + Trametinib 0.2 + 2 + 0.02 | Afatinib + Dabrafenib + Trametinib 0.04 + 0.4 + 0.004 |
| Dabrafenib + Palbociclib 2 + 0.5 | Dabrafenib + Palbociclib 0.4 + 0.1 | Erlotinib + Dabrafenib + Palbociclib 5 + 2 + 0.5 | Erlotinib + Dabrafenib + Palbociclib 1 + 0.4 + 0.1 | Afatinib + Dabrafenib + Palbociclib 0.2 + 2 + 0.5 | Afatinib + Dabrafenib + Palbociclib 0.04 + 0.4 + 0.1 |
| Trametinib + Palbociclib 0.02 + 0.5 | Trametinib + Palbociclib 0.004 + 0.1 | Erlotinib + Trametinib + Palbociclib 5 + 0.02 + 0.5 | Erlotinib + Trametinib + Palbociclib 1 + 0.004 + 0.1 | Afatinib + Trametinib + Palbociclib 0.2 + 0.02 + 0.5 | Afatinib + Trametinib + Palbociclib 0.04 + 0.004 + 0.1 |
| Dabrafenib + Trametinib + Palbociclib 2 + 0.02 + 0.5 | Dabrafenib + Trametinib + Palbociclib 0.4 + 0.004 + 0.1 | Erlotinib + Dabrafenib + Trametinib + Palbocilcib 5 + 2 + 0.02 + 0.5 | Erlotinib + Dabrafenib + Trametinib + Palbocilcib 1 + 0.4 + 0.004 + 0.1 | Afatinib + Dabrafenib + Trametinib + Palbociclib 0.2 + 2 + 0.02 + 0.5 | Afatinib + Dabrafenib + Trametinib + Palbociclib 0.04 + 0.4 + 0.004 + 0.1 |

| Osimertinib 2 | Osimertinib 0.4 | Cobimetinib 0.2 | Cobimetinib 0.04 |
|---|---|---|---|
| Osimertinib + Dabrafenib 2 + 2 | Osimertinib + Dabrafenib 0.4 + 0.4 | Selumetinib 2 | Selumetinib 0.4 |
| Osimertinib + Trametinib 2 + 0.02 | Osimertinib + Trametinib 0.4 + 0.004 | Lapatinib 10 | Lapatinib 2 |
| Osimertinib + Palbociclib 2 + 0.5 | Osimertinib + Palbociclib 0.4 + 0.1 | Vorinostat 1 | Vorinostat 0.2 |
| Osimertinib + Dabrafenib + Trametinib 2 + 2 + 0.02 | Osimertinib + Dabrafenib + Trametinib 0.4 + 0.4 + 0.004 | Olaparib 10 | Olaparib 2 |
| Osimertinib + Dabrafenib + Palbociclib 2 + 2 + 0.5 | Osimertinib + Dabrafenib + Palbociclib 0.4 + 0.4 + 0.1 | Everolimus 0.03 | Everolimus 0.006 |
| Osimertinib + Trametinib + Palbociclib 2 + 0.02 + 0.5 | Osimertinib + Trametinib + Palbociclib 0.4 + 0.004 + 0.1 | Crizotinib 0.3 | Crizotinib 0.06 |
| Osimertinib + Dabrafenib + Trametinib + Palbociclib 2 + 2 + 0.02 + 0.5 | Osimertinib + Dabrafenib + Trametinib + Palbociclib 0.4 + 0.4 + 0.004 + 0.1 | Osimertinib + Crizotinib 2 + 0.3 | Osimertinib + Crizotinib 0.4 + 0.06 |

Following exposure with drug, the epithelial tumor cells were labeled with 5-ethynyl-2'-deoxyuridine (Edu) to assess the tumor cell proliferation rates. The labeling lasted 24 hours in the presence of drug exposure. In the control group, epithelial tumor cells received no drug exposure with media change, but were similarly labeled with Edu. The labeled tumor cell were fixed and stained with Hoechst 33342 in blocking buffer containing 0.5% Triton X-100 and 3% BSA overnight at 4° C. The tumor cells were incubated with EpCAM antibody (1:4000) for 2 hours at room temperature and rinsed with PBST. Subsequently, the tumor cells were incubated with Alexa FluorR 647 conjugated goat-anti-mouse secondary antibody for 30 minutes at room temperature and rinsed with PBST.

The incorporated Edu was detected by Click-iT reaction where fixed cells were incubated with a reaction mixture containing 1× Click-iT Edu reaction buffer, CuSO4, and azide-conjugated Alexa Fluor dye in the dark. The stained cells were washed with PBS two times before image acquisition and analysis.

For image acquisition and analysis, the stained tumor cells were imaged by a high-content screening (HCS) platform (Thermo Scientific CellomicsArrayScanXTi HCS reader). The 10× objective was used to collect images. Twenty-five fields were imaged for each well for the analysis. From the images three fluorescent signals were obtained from the HCS reader. Blue fluorescent signals recorded nucleus signals stained with Hoechst 33342, green fluorescent signal detected the Edu incorporated in newly synthesized DNA, and red fluorescent signal detected the EpCAM positive epithelial cells population (see FIG. 1).

The MI (Maximum Inhibition Index) was calculated using the EpCAM and Edu positive readout (see Table E2 and Table E3 below).

TABLE E2

| Patient ID | Cancer type | Control EdU+ | E | E + D | E + T | E + P | E + D + T | E + D + P | E + T + P | E + D + T + P | E + C |
|---|---|---|---|---|---|---|---|---|---|---|---|
| NYL-102 | colon | 5876 | 11.79 | 3.34 | 123.96 | 30.18 | 58.82 | 19.99 | 309.74 | 172.72 | 20.59 |
| NYL-081 | colon | 16127 | 0.76 | 1.68 | 15.55 | 6.83 | 2.75 | 2.44 | 238.92 | 39.24 | 0.72 |
| NYL-088 | liver | 15032 | 61.79 | 11.63 | 5693.89 | 983.12 | 222.30 | 223.29 | 13918.39 | 9954.87 | 126.96 |
| CKY-016 | colon | 3095 | 2.32 | 3.24 | 271.22 | 10.27 | 20.73 | 8.99 | 87.49 | 49.63 | 1.74 |
| NYL-HZ-002 | colon | 3047 | 49.07 | 24.67 | 192.60 | 447.43 | 111.37 | 219.84 | 447.00 | 447.00 | 50.03 |
| ZKB-171 | colon | 8605 | 13.50 | 5.22 | 39.21 | 123.10 | 87.79 | 10.41 | 907.67 | 220.07 | 39.08 |
| NYL-109 | colon | 3810 | 67.63 | 21.85 | 451.43 | 1085.49 | 254.00 | 449.30 | 1085.00 | 1085.00 | 101.57 |
| NYL-178 | colon | 19624 | 1.82 | 2.15 | 2.69 | 10.25 | 4.46 | 7.07 | 214.47 | 279.07 | |
| NYL-JN-025 | colon | 5065 | 7.79 | 4.57 | 115.97 | 8.60 | 21.49 | 15.83 | 107.09 | 80.15 | 13.40 |
| NYL-149 | colon | 1498 | 2.18 | 2.95 | 140.79 | 6.18 | 10.77 | 5.20 | 561.03 | 50.59 | 3.82 |
| NYL-161 | colon | 27848 | 5.35 | 3.44 | 7.86 | 49.45 | 6.80 | 28.37 | 174.98 | 229.54 | 6.47 |
| NYL-132 | colon | 25722 | 1.19 | 9.37 | 110.04 | 2.69 | 956.90 | 42.00 | 440.44 | 813.97 | |
| NYL-113 | colon | 15034 | 3.58 | 2.77 | 65.15 | 32.23 | 21.23 | 9.95 | 239.78 | 124.20 | |
| NYL-170 | colon | 4512 | 0.81 | 1.20 | 3.83 | 2.14 | 1.46 | 1.70 | 38.92 | 13.11 | 0.77 |
| ZKB-070 | colon | 4765 | 18.49 | 7.78 | 55.34 | 1430.91 | 34.59 | 172.96 | 5015.73 | 5015.73 | 25.58 |
| NYP-006 | gastric | 1236 | 2.07 | 0.98 | 1.22 | 1.85 | 1.06 | 1.55 | 9.49 | 9.60 | 1.30 |
| NYL-040 | colon | 6000 | 10.06 | 8.74 | 64.88 | 194.75 | 39.67 | 144.94 | 2069.08 | 586.54 | 11.95 |
| ZKB-007 | colon | 6871 | 18.18 | 9.20 | 55.93 | 1861.97 | 38.94 | 302.41 | 6871.00 | 6871.00 | 33.29 |
| ZKB-165 | gastric | 3984 | 0.65 | 0.85 | 6.48 | 32.57 | 3.40 | 24.17 | 257.38 | 320.02 | 0.65 |
| ZKB-011 | pancrea | 12746 | 2.54 | 1.99 | 7.39 | 13.43 | 3.62 | 7.36 | 171.41 | 78.59 | 2.62 |
| NYL-053 | colon | 13107 | 11.48 | 7.45 | 84.80 | 143.21 | 16.96 | 36.64 | 1040.23 | 255.79 | 42.40 |
| NYL-171 | lung | 3471 | 7.97 | 3.33 | 155.25 | 158.08 | 13.65 | 26.95 | 3337.84 | 396.73 | 11.77 |

E, EGFR inhibitor;
D, BRAF inhibitor;
T, MEK1/2 inhibitor;
P CDK4/6 inhibitor;
C, c-MET inhibitor

TABLE E3

| Patient ID | Cancer type | Control EdU+ | D | T | P | D + T | D + P | T + P | D + T + P |
|---|---|---|---|---|---|---|---|---|---|
| NYL-102 | colon | 5876 | | | | 1.81 | 2.58 | 4.44 | 2.83 |
| NYL-081 | colon | 16127 | | | | 0.93 | 2.18 | 5.68 | 2.63 |
| NYL-088 | liver | 15032 | | | | 1.39 | 2.69 | 2.81 | 1.39 |
| CKY-016 | colon | 3095 | | | | 4.43 | 3.20 | 98.06 | 17.12 |
| NYL-HZ-002 | colon | 3047 | 0.83 | 2.06 | 2.10 | 2.02 | 2.08 | 4.11 | 3.40 |
| CKY-041 | colon | 12553 | | 1.05 | 1.10 | 0.90 | 1.64 | 1.01 | 1.14 |
| ZKB-171 | colon | 8605 | 1.18 | 1.85 | 1.43 | 1.46 | 1.81 | 3.92 | 2.77 |
| NYL-109 | colon | 3810 | 1.52 | 7.57 | 1.68 | 5.45 | 1.41 | 6.46 | 3.42 |
| NYL-178 | colon | 19624 | | | | | | | |
| NYL-JN-025 | colon | 5065 | | | | 3.56 | 3.13 | 4.37 | 4.13 |
| NYL-149 | colon | 1498 | 4.01 | 4.13 | 2.35 | 0.59 | 5.23 | 4.28 | 1.59 |
| NYL-161 | colon | 27848 | 0.94 | 1.01 | 1.35 | 0.96 | 1.39 | 1.43 | 1.62 |
| NYL-132 | colon | 25722 | 1.42 | 1.42 | 1.94 | 2.45 | 2.88 | 2.40 | 3.97 |
| NYL-113 | colon | 15034 | 0.96 | 1.86 | 1.79 | 1.12 | 1.21 | 3.98 | 1.88 |
| NYL-170 | colon | 4512 | 2.11 | 0.61 | 3.09 | 0.51 | 5.68 | 0.89 | 0.93 |
| ZKB-070 | colon | 4765 | 1.18 | 0.74 | 4.35 | 0.73 | 3.29 | 1.72 | 1.23 |
| NYP-006 | gastric | 1236 | 0.47 | 0.55 | 2.89 | 0.35 | 1.16 | 0.86 | 0.79 |
| NYL-040 | colon | 6000 | 1.08 | 0.85 | 6.68 | 0.57 | 4.82 | 3.02 | 2.99 |
| ZKB-007 | colon | 6871 | 0.91 | 0.76 | 3.00 | 0.69 | 2.93 | 2.37 | 1.60 |
| ZKB-165 | gastric | 3984 | 1.83 | 0.60 | 7.38 | 0.63 | 9.15 | 8.00 | 13.40 |
| ZKB-011 | pancrea | 12746 | 1.00 | 1.08 | 6.85 | 0.73 | 5.44 | 20.42 | 17.06 |
| NYL-053 | colon | 13107 | 1.10 | 1.96 | 2.71 | 1.36 | 1.90 | 5.00 | 2.48 |

E, EGFR inhibitor;
D, BRAF inhibitor;
T, MEK1/2 inhibitor;
P CDK4/6 inhibitor;
C, c-MET inhibitor MI (Maximum Inhibition Index)=Edu positive cells in control/Edu positive cells in Treatment.

The inhibition percentage was calculated using the EpCAM and Edu positive readout as follows (see Table E4 and Table E5 below).

TABLE E4

| Patient ID | Cancer type | Cntrl. EdU+ | E | E + D | E + T | E + P | E + D + T | E + D + P | E + T + P | E + D + T + P | E + C |
|---|---|---|---|---|---|---|---|---|---|---|---|
| NYL-102 | colon | 5876 | | | | | | | | | |
| NYL-081 | colon | 16127 | 91.52% | 70.03% | 99.19% | 96.69% | 98.30% | 95.00% | 99.68% | 99.42% | 95.14% |
| NYL-088 | liver | 15032 | 0.00% | 40.42% | 93.57% | 85.37% | 63.59% | 58.97% | 99.58% | 97.45% | 0.00% |
| CKY-016 | colon | 3095 | 98.38% | 91.40% | 99.98% | 99.90% | 99.55% | 99.55% | 99.99% | 99.99% | 99.21% |
| NYL-HZ-002 | colon | 3047 | 56.85% | 69.12% | 99.63% | 90.27% | 95.18% | 88.87% | 98.86% | 97.99% | 42.66% |
| CKY-041 | colon | 12553 | 97.96% | 95.95% | 99.48% | 99.78% | 99.10% | 99.55% | 99.78% | 99.78% | 98.00% |
| ZKB-171 | colon | 8605 | 0.00% | 100.00% | 77.58% | 70.98% | 59.45% | 39.82% | 96.07% | 79.35% | 0.00% |
| NYL-109 | colon | 3810 | 92.59% | 80.85% | 97.45% | 99.19% | 98.86% | 90.40% | 99.89% | 99.55% | 97.44% |
| NYL-178 | colon | 19624 | 98.52% | 95.42% | 99.78% | 99.91% | 99.61% | 99.78% | 99.91% | 99.91% | 99.02% |
| NYL-JN-025 | colon | 5065 | 45.19% | 53.44% | 62.79% | 90.24% | 77.60% | 85.86% | 99.53% | 99.64% | |
| NYL-149 | colon | 1498 | 87.17% | 78.10% | 99.14% | 88.38% | 95.35% | 93.68% | 99.07% | 98.75% | 92.54% |
| NYL-161 | colon | 27848 | 54.23% | 66.12% | 99.29% | 83.82% | 90.72% | 80.78% | 99.82% | 98.02% | 73.82% |
| NYL-132 | colon | 25722 | 81.30% | 70.90% | 87.27% | 97.98% | 85.30% | 96.47% | 99.43% | 99.56% | 84.55% |
| NYL-113 | colon | 15034 | 15.74% | 89.33% | 99.09% | 62.77% | 99.90% | 97.62% | 99.77% | 99.88% | |
| NYL-170 | colon | 4512 | 72.06% | 63.84% | 98.47% | 96.90% | 95.29% | 89.95% | 99.58% | 99.19% | |
| ZKB-070 | colon | 4765 | 0.00% | 16.37% | 73.87% | 53.16% | 31.43% | 41.25% | 97.43% | 92.37% | 0.00% |
| NYP-006 | gastric | 1236 | 94.59% | 87.15% | 98.19% | 99.93% | 97.11% | 99.42% | 99.98% | 99.98% | 96.09% |
| NYL-040 | colon | 6000 | 51.75% | −2.54% | 18.31% | 46.01% | 5.55% | 35.42% | 89.46% | 89.58% | 23.26% |
| ZKB-007 | colon | 6871 | 90.06% | 88.56% | 98.46% | 99.49% | 97.48% | 99.31% | 99.95% | 99.83% | 91.63% |
| ZKB-165 | gastric | 3984 | 94.50% | 89.13% | 98.21% | 99.95% | 97.43% | 99.67% | 99.99% | 99.99% | 97.00% |
| ZKB-011 | pancrea | 12746 | 0.00% | 0.00% | 84.57% | 96.93% | 70.61% | 95.86% | 99.61% | 99.69% | 0.00% |
| NYL-053 | colon | 13107 | 60.61% | 49.87% | 86.46% | 92.55% | 72.39% | 86.41% | 99.42% | 98.73% | 61.79% |

E, EGFR inhibitor;
D, BRAF inhibitor;
T, MEK1/2 inhibitor;
P CDK4/6 inhibitor;
C, c-MET inhibitor

TABLE E5

| Patient ID | Cancer type | Control EdU+ | D | T | P | D + T | D + P | T + P | D + T + P |
|---|---|---|---|---|---|---|---|---|---|
| NYL-102 | colon | 5876 | | | | 44.87% | 61.27% | 77.49% | 64.68% |
| NYL-081 | colon | 16127 | | | | 0.00% | 54.05% | 82.38% | 61.97% |
| NYL-088 | liver | 15032 | | | | 27.88% | 62.76% | 64.39% | 27.80% |
| CKY-016 | colon | 3095 | | | | 77.43% | 68.76% | 98.98% | 94.16% |
| NYL-HZ-002 | colon | 3047 | 0.00% | 51.53% | 52.48% | 50.56% | 51.99% | 75.66% | 70.61% |
| CKY-041 | colon | 12553 | | 5.05% | 9.05% | 0.00% | 39.07% | 0.56% | 12.42% |
| ZKB-171 | colon | 8605 | 15.07% | 46.02% | 30.13% | 31.67% | 44.81% | 74.51% | 63.87% |
| NYL-109 | colon | 3810 | 34.25% | 86.79% | 40.42% | 81.65% | 28.85% | 84.52% | 70.73% |
| NYL-178 | colon | 19624 | | | | | | | |
| NYL-JN-025 | colon | 5065 | | | | 71.95% | 68.06% | 77.12% | 75.78% |
| NYL-149 | colon | 1498 | 75.06% | 75.78% | 57.40% | 0.00% | 80.86% | 76.61% | 37.06% |
| NYL-161 | colon | 27848 | −6.33% | 0.59% | 26.16% | 0.00% | 27.82% | 30.25% | 38.17% |
| NYL-132 | colon | 25722 | 29.59% | 29.60% | 48.53% | 59.20% | 65.24% | 58.39% | 74.82% |
| NYL-113 | colon | 15034 | −3.84% | 46.31% | 44.25% | 10.74% | 17.53% | 74.90% | 46.70% |
| NYL-170 | colon | 4512 | 52.58% | 0.00% | 67.64% | 0.00% | 82.40% | 0.00% | 0.00% |
| ZKB-070 | colon | 4765 | 15.53% | −34.50% | 77.00% | 0.00% | 69.60% | 41.91% | 18.51% |
| NYP-006 | gastric | 1236 | 0.00% | 0.00% | 65.36% | 0.00% | 13.84% | 0.00% | 0.00% |
| NYL-040 | colon | 6000 | 7.18% | 0.00% | 85.02% | 0.00% | 79.24% | 66.85% | 66.51% |
| ZKB-007 | colon | 6871 | 0.00% | 0.00% | 66.72% | 0.00% | 65.86% | 57.89% | 37.46% |
| ZKB-165 | gastric | 3984 | 45.31% | 0.00% | 86.45% | 0.00% | 89.07% | 87.51% | 92.54% |
| ZKB-011 | pancrea | 12746 | 0.00% | 7.36% | 85.40% | 0.00% | 81.61% | 95.10% | 94.14% |
| NYL-053 | colon | 13107 | 9.11% | 49.02% | 63.04% | 26.59% | 47.25% | 79.99% | 59.60% |

E, EGFR inhibitor;
D, BRAF inhibitor;
T, MEK1/2 inhibitor;
P CDK4/6 inhibitor;
C, c-MET inhibitor Inhibition percentage for drug A (AI)=1-Edu positive cells in A treatment/Edu positive cells in control.

Inhibition percentage for drug AB (ABI)=1-Edu positive cells in AB treatment/Edu positive cells in control.

Inhibition percentage for drug ABC (ABCI)=1-Edu positive cells in ABC treatment/Edu positive cells in control.

The combinational index at the AUC concentration for drug combinations was calculated using the Bliss Independence model under effect-based strategy (see Table E6 below).

TABLE E6

| Patient ID | Cancer type | E + D | E + T | E + P | E + D + T | E + D + P | E + T + P | E + D + T + P | E + C | D + T | D + P | T + P | D + T + P |
|---|---|---|---|---|---|---|---|---|---|---|---|---|---|
| NYL-HZ-002 | colon | 1.99 | 0.53 | 0.23 | 0.91 | 0.47 | 0.48 | 0.48 | 0.98 | 1.02 | 1.01 | 1.06 | 1.28 |
| CKY-041 | colon |  | 0.24 | 0.32 |  |  |  | 0.05 |  | 1.00 |  | 1.15 |  |
| ZKB-171 | colon | 3.04 | 0.64 | 0.16 | 0.34 | 2.18 | 0.04 | 0.19 | 0.40 | 1.49 | 0.93 | 0.68 | 1.13 |
| NYL-109 | colon | 4.71 | 1.13 | 0.10 | 3.06 | 0.38 | 0.79 | 1.20 | 0.97 | 2.11 | 1.82 | 1.97 | 5.65 |
| NYL-149 | colon | 2.97 | 0.06 | 0.83 | 3.36 | 3.95 | 0.04 | 1.68 | 0.57 | 16.56 | 1.80 | 2.27 | 24.46 |
| NYL-161 | colon | 1.56 | 0.68 | 0.15 | 0.79 | 0.26 | 0.04 | 0.03 | 0.83 | 1.01 | 0.98 | 0.95 | 0.84 |
| NYL-132 | colon | 0.18 | 0.02 | 0.86 | 0.00 | 0.08 | 0.01 | 0.01 |  | 0.82 | 0.96 | 1.15 | 0.99 |
| NYL-113 | colon | 1.29 | 0.10 | 0.20 | 0.31 | 0.65 | 0.05 | 0.10 |  | 1.66 | 1.48 | 0.84 | 1.78 |
| NYL-170 | colon | 1.76 | 0.26 | 1.45 | 1.45 | 3.83 | 0.08 | 0.50 | 1.00 | 2.11 | 1.15 | 3.09 | 6.52 |
| ZKB-070 | colon | 2.81 | 0.33 | 0.06 | 0.63 | 0.55 | 0.02 | 0.02 | 0.72 | 1.18 | 1.56 | 2.53 | 4.19 |
| NYP-006 | gastric | 2.07 | 1.69 | 3.23 | 1.96 | 3.86 | 0.63 | 0.62 | 1.59 | 1.00 | 2.49 | 2.89 | 2.89 |
| NYL-040 | colon | 1.24 | 0.16 | 0.34 | 0.27 | 0.50 | 0.03 | 0.12 | 0.84 | 1.08 | 1.49 | 2.21 | 2.41 |
| ZKB-007 | colon | 1.98 | 0.33 | 0.03 | 0.47 | 0.18 | 0.01 | 0.01 | 0.60 | 1.00 | 1.03 | 1.27 | 1.88 |
| ZKB-165 | gastric | 1.83 | 0.15 | 0.23 | 0.54 | 0.56 | 0.03 | 0.04 | 1.31 | 1.83 | 1.47 | 0.92 | 1.01 |
| ZKB-011 | pancrea | 1.27 | 0.37 | 1.29 | 0.76 | 2.36 | 0.11 | 0.24 | 1.03 | 1.08 | 1.26 | 0.36 | 0.43 |
| NYL-053 | colon | 1.70 | 0.27 | 0.22 | 1.46 | 0.93 | 0.06 | 0.26 | 0.39 | 1.58 | 1.57 | 1.06 | 2.36 |
| NYL-171 | lung | 3.71 | 0.05 | 0.15 | 0.95 | 1.33 | 0.01 | 0.10 | 0.74 | 1.63 | 1.55 | 1.02 | 2.13 |

E, EGFR inhibitor;
D, BRAF inhibitor;
T, MEK1/2 inhibitor;
P CDK4/6 inhibitor;
C, c-MET inhibitor $$CI(AB)=(AI+BI-AI*BI)/(ABI).$$

The combinational index at the AUC concentration for drug triple combinations were calculated using Bliss Independence model under effect-based strategy.

$$CI(ABC)=(AI+BI+CI-AI*BI-AI*CI-BI*CI+AI*BI*CI)/(ABCI)$$

If CI<1, the combination of A and B is synergistic.
If CI=1, the combination of A and B is additive.
if CI>1, the combination of A and B is antagonistic.

These results illustrate that various combinations of EGFR, MEK 1/2, and/or CDK 4/6 inhibitors provide significantly increased (e.g., synergistically-increased) tumor-cell killing activity in an ex vivo model of primary tumor cells of a variety of tissues, including colon, gastric, pancreatic, and lung tissues, among others.

The invention claimed is:

1. A method of treating a cancer in a subject in need thereof, comprising administering to the subject a combination of:
   (a) an epidermal growth factor receptor (EGFR) inhibitor selected from one or more of erlotinib, gefitinib, afatinib, lapatinib, osimertinib, brigatinib, and icotinib;
   (b) a mitogen-activated protein kinase (MEK) 1/2 inhibitor selected from one or more of trametinib, selumetinib, and cobimetinib; and
   (c) a cyclin dependent kinase (CDK) 4/6 inhibitor selected from one or more of palbociclib, ribociclib, and abemaciclib.

2. The method of claim 1, comprising administering the combination of (a), (b), and (c) to the subject, together as part of the same composition.

3. The method of claim 1, comprising administering the combination of (a), (b), and (c) to the subject, as separate compositions.

4. The method of claim 1, wherein the cancer is a malignant epithelial tumor or carcinoma.

5. The method of claim 4, wherein the carcinoma is selected from one or more of an adenocarcinoma, a squamous cell carcinoma, an adenosquamous carcinoma, an anaplastic carcinoma, a large cell carcinoma, and a small cell carcinoma.

6. The method of claim 4, wherein the carcinoma is selected from one or more of an epithelial neoplasm, a squamous cell neoplasm (squamous cell carcinoma), a basal cell neoplasm (basal cell carcinoma), a transitional cell carcinoma, an adenocarcinoma (optionally a linitis plastica, a vipoma, a cholangiocarcinoma, a hepatocellular carcinoma, an adenoid cystic carcinoma, a renal cell carcinoma, or a Grawitz tumor), an adnexal or skin appendage neoplasm, a nucoepidermoid neoplasm, a cystic, mucinous, or Serous Neoplasm, a ductal, lobular, or medullary Neoplasm, an accinar cell neoplasm, and a complex epithelial neoplasm.

7. The method of claim 1, wherein the cancer is a carcinoma selected from one or more of a colon or colorectal cancer, a gastric cancer, a lung cancer (optionally small cell lung cancer or non-small lung cell cancer), a breast cancer, a pancreatic cancer, an oral cancer, a prostate cancer, a germline cancer, a rectal cancer, a liver cancer (optionally hepatocellular carcinoma), a kidney cancer (optionally renal cell carcinoma), and an ovarian cancer.

8. The method of claim 1, wherein the combination of (a), (b), and (c) reduces cancer cell growth by about or at least about 5, 10, 15, 20, 25, 30, 35, 40, 45, 50, 60, 70, 80, 90, 100, 200, 300, 400, 500, 600, 700, 800, 900, 1000, 2000% or more relative to (a), (b), and/or (c) alone.

9. The method of claim 8, wherein the combination of (a), (b), and (c) synergistically reduces cancer cell growth and/or synergistically increases cancer cell-killing relative to (a), (b), and/or (c) alone.

* * * * *